US012573482B2

(12) United States Patent
Araki et al.

(10) Patent No.: US 12,573,482 B2
(45) Date of Patent: Mar. 10, 2026

(54) DECISION APPARATUS, DECISION METHOD, AND COMPUTER READABLE MEDIUM

(71) Applicants: NEC CORPORATION, Tokyo (JP); Kagoshima Medical IT Center Co., Ltd., Kagoshima (JP)

(72) Inventors: Kenji Araki, Tokyo (JP); Yutaka Uno, Tokyo (JP); Yuki Kusano, Tokyo (JP); Yumiko Uto, Kagoshima (JP)

(73) Assignees: NEC Corporation, Minato-ku (JP); Kagoshima Medical IT Center Co., Ltd., Kagoshima (JP)

( * ) Notice: Subject to any disclaimer, the term of this patent is extended or adjusted under 35 U.S.C. 154(b) by 257 days.

(21) Appl. No.: 18/364,170

(22) Filed: Aug. 2, 2023

(65) Prior Publication Data

US 2024/0047030 A1     Feb. 8, 2024

(30) Foreign Application Priority Data

Aug. 3, 2022     (JP) ................................. 2022-124027

(51) Int. Cl.
G16H 15/00          (2018.01)
G08B 21/18          (2006.01)
(52) U.S. Cl.
CPC ........... G16H 15/00 (2018.01); G08B 21/182 (2013.01)

(58) Field of Classification Search
CPC ........ G16H 15/00; G16H 30/40; G16H 50/20; G08B 21/182
See application file for complete search history.

(56) References Cited

U.S. PATENT DOCUMENTS

2019/0246973 A1*   8/2019   Constantin ............. G16H 40/67
2020/0273572 A1*   8/2020   Kartoun ................. G06F 40/30
2021/0391047 A1*   12/2021  Mura .................... G16H 10/20
2023/0072095 A1*   3/2023   Krüger .................. G16H 30/40

FOREIGN PATENT DOCUMENTS

JP          2019-008816 A          1/2019

* cited by examiner

*Primary Examiner* — Cao H Nguyen
(74) *Attorney, Agent, or Firm* — Sughrue Mion, PLLC

(57) ABSTRACT

The decision apparatus according to one example embodiment of the present disclosure includes at least one memory configured to store an instruction, and at least one processor configured to execute the instruction. The processor executes the instruction, and thereby calculates a degree of necessity of generation of a document relating to a decision target person, by inputting state information of the decision target person with respect to a learning model being learned by using learning data including state information of a person and information indicating whether generation of the document relating to the person is necessary or unnecessary, and decides whether to output an alert related to document generation of the decision target person, by using the calculated degree of necessity and information indicating whether the document is actually generated for the decision target person.

13 Claims, 23 Drawing Sheets

10

|  | HISTORY OF DOCUMENT GENERATION (OBJECTIVE VARIABLE) | | STATE INFORMATION OF PATIENT (EXPLANATORY VARIABLE) | | | |
| NUMBER OF DAYS | PRESENCE OR ABSENCE OF GENERATION OF DOCUMENT 1 | PRESENCE OR ABSENCE OF GENERATION OF DOCUMENT 2 | BODY TEMPERATURE | AGE | NURSING RECORD | |
|---|---|---|---|---|---|---|
| PATIENT A | FIRST DAY | 1 | 0 | 36.7°C | 50 YEARS OLD | (0.1, 0.5, 0.2, ...) | ... |
| PATIENT A | SECOND DAY | 0 | 1 | 36.5°C | 50 YEARS OLD | (0.3, 0.1, 0.7, ...) | ... |
| PATIENT B | FIRST DAY | 0 | 0 | 35.9°C | 70 YEARS OLD | (0.6, 0.2, 0.3, ...) | ... |
| PATIENT B | SECOND DAY | 1 | 0 | 35.8°C | 70 YEARS OLD | (0.9, 0.6, 0.5, ...) | ... |

Fig. 7

| ITEM | DESCRIPTION CONTENT |
|---|---|
| PRESENCE OR ABSENCE OF BEDSORE | ABSENCE, PRESENCE |
| SITE WHERE BEDSORE OCCURS | SACRAL REGION, COCCYGEAL REGION, RIGHT ISCHIUM REGION, LEFT ISCHIUM REGION, OR THE LIKE |
| SITE WHERE BEDSORE IS LIKELY TO OCCUR IN FUTURE | SACRAL REGION, COCCYGEAL REGION, RIGHT ISCHIUM REGION, LEFT ISCHIUM REGION, OR THE LIKE |
| MATTRESS | (MATERIAL OR MANUFACTURER) |
| MEASURE CONTENT BY MEDICAL PROFESSIONAL | MEASUREMENT OF BODY PRESSURE, TYPE OF TOOL TO BE USED, OR THE LIKE |
| USE OF MEDICINE AFFECTING OCCURRENCE OF BEDSORE | ABSENCE, PRESENCE (WHEN PRESENCE, TYPE) |

Fig. 16

| PATIENT | HISTORY OF DOCUMENT GENERATION (EXPLANATORY VARIABLE) | DESCRIPTION CONTENT FOR EACH ITEM OF DOCUMENT (OBJECTIVE VARIABLE) | STATE INFORMATION OF PATIENT (EXPLANATORY VARIABLE) | | | |
|---|---|---|---|---|---|---|
| | NUMBER OF DAYS | PRESENCE OR ABSENCE OF GENERATION OF DOCUMENT 1 | DESCRIPTION CONTENT FOR EACH ITEM OF DOCUMENT 1 | BODY TEMPERATURE | AGE | NURSING RECORD | ... |
| PATIENT A | FIRST DAY | 1 | (0.4, 0.3, 0.1...) | 36.7°C | 50 YEARS OLD | (0.1, 0.5, 0.2...) | ... |
| PATIENT A | SECOND DAY | 0 | - | 36.5°C | 50 YEARS OLD | (0.3, 0.1, 0.7...) | ... |
| PATIENT B | FIRST DAY | 0 | - | 35.9°C | 70 YEARS OLD | (0.6, 0.2, 0.3...) | ... |
| PATIENT B | SECOND DAY | 1 | (0.7, 0.8, 0.4...) | 35.8°C | 70 YEARS OLD | (0.9, 0.6, 0.5...) | ... |

Fig. 17

DECISION APPARATUS, DECISION METHOD, AND COMPUTER READABLE MEDIUM

INCORPORATION BY REFERENCE

This application is based upon and claims the benefit of priority from Japanese patent application No. 2022-124027, filed on Aug. 3, 2022, the disclosure of which is incorporated herein in its entirety by reference.

TECHNICAL FIELD

The present disclosure relates to a decision apparatus, a decision method, and a program.

BACKGROUND ART

A technique for reducing a burden on a medical professional has been developed in a medical field. For example, Japanese Unexamined Patent Application Publication No. 2019-008816 describes a technique of a support apparatus that alerts a doctor to omission of description with respect to an area not described in a report sentence in spite of an area that the doctor has been gazing at in medical image data.

SUMMARY

From a viewpoint of providing high-quality medical care to a patient or a viewpoint of satisfying a requirement necessary for a medical institution, the medical institution may need to generate a document of specific type depending on a state of a patient. However, such a document may not be properly generated due to prioritization of medical care to a patient. In this case, administrative investigation decides that a requirement of medical care is not properly satisfied, and there is a risk that the medical institution must return a medical treatment fee.

An example object of the disclosure is to provide a decision apparatus, a decision method, and a program that are useful for prompting to appropriately perform document generation relating to a decision target person.

In a first example aspect of the present disclosure, a decision apparatus includes at least one memory configured to store an instruction, and at least one processor configured to execute the instruction. The processor executes the instruction, thereby calculates a degree of necessity of generation of a document relating to a decision target person, by inputting state information of the decision target person with respect to a learning model being learned by using learning data including state information of a person and information indicating whether generation of the document relating to the person is necessary or unnecessary, and decides whether to output an alert related to document generation of the decision target person, by using the calculated degree of necessity and information indicating whether the document is actually generated for the decision target person.

In a second example aspect of the present disclosure, a decision method includes, by a computer: calculating a degree of necessity of generation of a document relating to a decision target person, by inputting state information of the decision target person with respect to a learning model being learned by using learning data including state information of a person and information indicating whether generation of the document relating to the person is necessary or unnecessary; and deciding whether to output an alert related to document generation of the decision target person, by using the calculated degree of necessity and information indicating whether the document is actually generated for the decision target person.

In a third example aspect of the present disclosure, a non-transitory computer readable medium stores a program causing a computer to execute: calculating a degree of necessity of generation of a document relating to a decision target person, by inputting state information of the decision target person with respect to a learning model being learned by using learning data including state information of a person and information indicating whether generation of the document relating to the person is necessary or unnecessary; and deciding whether to output an alert related to document generation of the decision target person, by using the calculated degree of necessity and information indicating whether the document is actually generated for the decision target person.

BRIEF DESCRIPTION OF DRAWINGS

The above and other aspects, features and advantages of the present disclosure will become more apparent from the following description of certain example embodiments when taken in conjunction with the accompanying drawings, in which:

FIG. 7 is a table illustrating one example of first learning data according to the disclosure;

FIG. 16 is a table illustrating examples of a description content for each item in a bedsore plan;

FIG. 17 is a table illustrating one example of second learning data generated by a learning data preprocessing unit according to the disclosure;

EXAMPLE EMBODIMENT

Hereinafter, example embodiments will be described with reference to the drawings. Note that, the following description and drawings are omitted and simplified as appropriate for clarity of description. Further, it should be noted that the drawings referred to for explanation in each embodiment are applicable to the other embodiment as well. In addition, in the present disclosure, unless otherwise specified, when "at least any of a plurality of items" is defined for the item, the definition may mean any one item in the plurality of items, or may mean any two or more items (including all items) in the plurality of items.

First Example Embodiment (1A)

Hereinafter, a first example embodiment of the present disclosure will be described with reference to the drawings. In (1A), a decision apparatus capable of deciding an output of an alert related to document generation will be described. [Description of Configuration]

Figure 1:
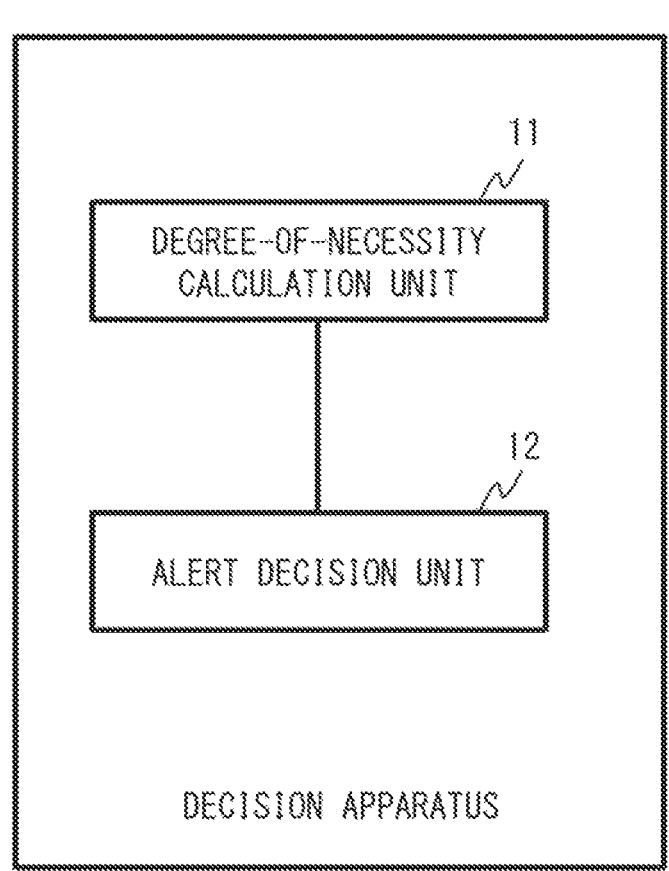
FIG. 1 is a block diagram illustrating one example of a decision apparatus according to the disclosure.

FIG. 1 is a block diagram illustrating one example of a decision apparatus. A decision apparatus 10 includes a degree-of-necessity calculation unit 11 and an alert decision unit 12. Each unit (each means) of the decision apparatus 10 is controlled by a not-illustrated control unit (controller). Hereinafter, each unit will be described.

The degree-of-necessity calculation unit 11 calculates a degree of necessity of generation of a document relating to a person (hereinafter, referred to as a decision target person) to be decided as an alert by inputting state information of the decision target person with respect to a predetermined learning model. The learning model is a model learned by using learning data including state information of a certain person and information indicating whether generation of the document relating to the person is necessary or unnecessary. Specifically, the learning data are data for machine learning relating to a person, includes state information of one or more persons as an explanatory variable, and includes information indicating whether document generation relating to the person is necessary or unnecessary as an objective variable associated to the explanatory variable. The learning data include a plurality of samples in which an explanatory variable and an objective variable become a set.

The state information of a person includes any one or plurality of types of information that can directly or indirectly indicate a physical state of the person. The state information may include at least any of pieces of structured data or unstructured data. The structured data are any pieces of data being converted into a numeral, and information such as age, gender, a vital sign, an examination value, a self-reported value, and a frequency of implementation of care of a person is equivalent to, for example. The self-reported value includes, for example, information such as a sleep time, and a physical condition being subjectively sensed and converted into a numeral. On the other hand, the unstructured data are equivalent to information such as a document such as a nursing record being recorded in natural language, an image, and a sound. The image includes, for example, an image of medical imaging (an image by visible light, an X-ray, magnetic resonance imaging (MRI), and the like), an image of a meal, and an image related to excretion. The sound includes, for example, a sound record of a state of a person by a doctor, a nurse, or a care worker, or a sound of a person. The state information of a person in this manner is, for example, state information of a patient in medical care or nursing, or state information of a care user.

A document relating to a person is any document of one or a plurality of types related to the person, for example, a document relating to at least any of medical care, nursing, or care of the person, and refers to a document being required to be generated when the person is in a predetermined state, or a document being recommended to be generated. The predetermined state refers to, for example, a case where a person has a predetermined injury or disease, or a symptom, or a case where presence of such a state is suspected.

The learning data include the above-described state information and information indicating whether document generation is necessary or unnecessary for a person to be learned. Therefore, the learning model learns, by using the learning data, whether a degree of necessity of document generation is high (or low) when a person is in what state. Any technique can be used to generate the learning model, and as one example, any of logistic regression, a support vector machine (SVM), or a neural network can be used. The degree-of-necessity calculation unit 11 inputs state information of a decision target person as an explanatory variable to the learned learning model, and thereby causes a degree of necessity of generation of a document relating to the decision target person to be calculated as an objective variable. The state information may be converted into a format suitable for learning before being input to the learning model.

Note that, a degree of necessity to be calculated may be information such as a numerical value expressed quantitatively, or may be information in a qualitative format. The quantitatively expressed information may be, for example, a binary value indicating whether it is necessary or unnecessary, or may be represented by a discrete numerical value of three or more values or a continuous numerical value indicating the degree of necessity. A numerical value of three or more values may indicates a probability indicating at least any of necessary or unnecessary of generation of a document. Note that, the learning model or the degree-of-necessity calculation unit 11 may calculate a numerical value acquired by logit-converting the probability and set the calculated numerical value as a degree of necessity. In addition, as an example of information on a degree of necessity in a qualitative format, it is assumed that "document generation is necessary", "document generation may be necessary", "document generation is not considered to be necessary", and "document generation is unnecessary". In this example, as the former becomes the latter, the degree of necessity of document generation decreases. However, the degree of necessity to be calculated is not limited thereto. The degree-of-necessity calculation unit 11 executes inference processing in this manner.

In addition, the degree of necessity to be calculated may be a degree of necessity of document generation of a decision target person at a calculation time point. Alternatively, in spite thereof or in addition thereto, the degree of necessity to be calculated may be a degree of necessity of document generation of the decision target person at a time point at least any of in future or in past from the calculation time point. The future or the past from the calculation time point means, for example, the future or the past within a predetermined period of time from the calculation time point, but is not limited thereto.

The alert decision unit 12 decides whether to output an alert related to document generation of a decision target person, by using a degree of necessity of document generation relating to the decision target person calculated by the degree-of-necessity calculation unit 11 and information indicating whether a document is actually generated for the decision target person. Specifically, the alert decision unit 12 decides that the document generation of the decision target person is necessary and outputs an alert, when the document is not actually generated for the decision target person and the calculated degree of necessity of document generation relating to the decision target person is a predetermined value or predetermined information.

When the degree of necessity to be calculated is the degree of necessity of document generation of the decision target person at the calculation time point, the alert decision unit 12 decides whether to output an alert related to document generation of the decision target person, by using, for example, information indicating whether a document being valid at the calculation time point for the decision target person has actually been generated. A document being valid at the calculation time point means, for example, that the generated document satisfies a predetermined requirement or that the document has been generated in the past within a predetermined period (within an expiration date) from the calculation time point.

For example, it is assumed that a degree of necessity is represented by any of two values of "necessary" and "unnecessary", and it is assumed that the document is not actually generated for the decision target person, and that the degree of necessity of document generation at the calculation time point relating to the decision target person is "necessary". At this time, the alert decision unit 12 decides that document generation of the decision target person is necessary. As another example, it is assumed that the degree of necessity is represented by any of three values or more, and it is assumed that the document is not actually generated for the decision target person, and that the degree of necessity of document generation at the calculation time point relating to the decision target person is equal to or more than a predetermined stage. At this time, the alert decision unit 12 decides that document generation of the decision target person is necessary.

In addition, when the degree of necessity to be calculated is the degree of necessity of document generation of the decision target person in the future from the calculation time point, the alert decision unit 12 decides whether to output an alert related to document generation of the decision target person, for example, by using information indicating whether a document being valid at a future timing for the decision target person has actually been generated. A document being valid at a future timing means, for example, that the generated document satisfies a predetermined requirement or that the document has been generated in the past within a predetermined period (within an expiration date) from the future timing.

In addition, when the degree of necessity to be calculated is the degree of necessity of document generation of the decision target person in the past from the calculation time point, the alert decision unit 12 decides whether to output an alert related to document generation of the decision target person, for example, by using information indicating whether a document being valid at a past timing for the decision target person has actually been generated. The document being valid at a past timing means, for example, that the generated document satisfies a predetermined requirement or that the document has been generated in the past within a predetermined period (within an expiration date) from the past timing.

Note that, a notification unit capable of notifying a user of an alert by at least display, sound, or the like is provided inside or outside the decision apparatus 10. The notification unit is constituted of, for example, a display, a speaker, and the like. The alert decision unit 12 outputs an alert to the notification unit, and thereby the notification unit issues an alert to a user.

Note that, in the first example embodiment, a "person" or a "decision target person" may be, for example, a patient being subject of a medical action, a care receiver being subject of care, or the like, but a subject being the "person" or the "decision target person" is not limited to these persons. In addition, a user of the decision apparatus 10 may be, for example, a medical professional, a care worker, or the like, but a subject of the user is not limited to these persons. Note that, a specific example of the medical professional is a doctor, a nurse, or the like.

[Description of Processing]

Figure 2:
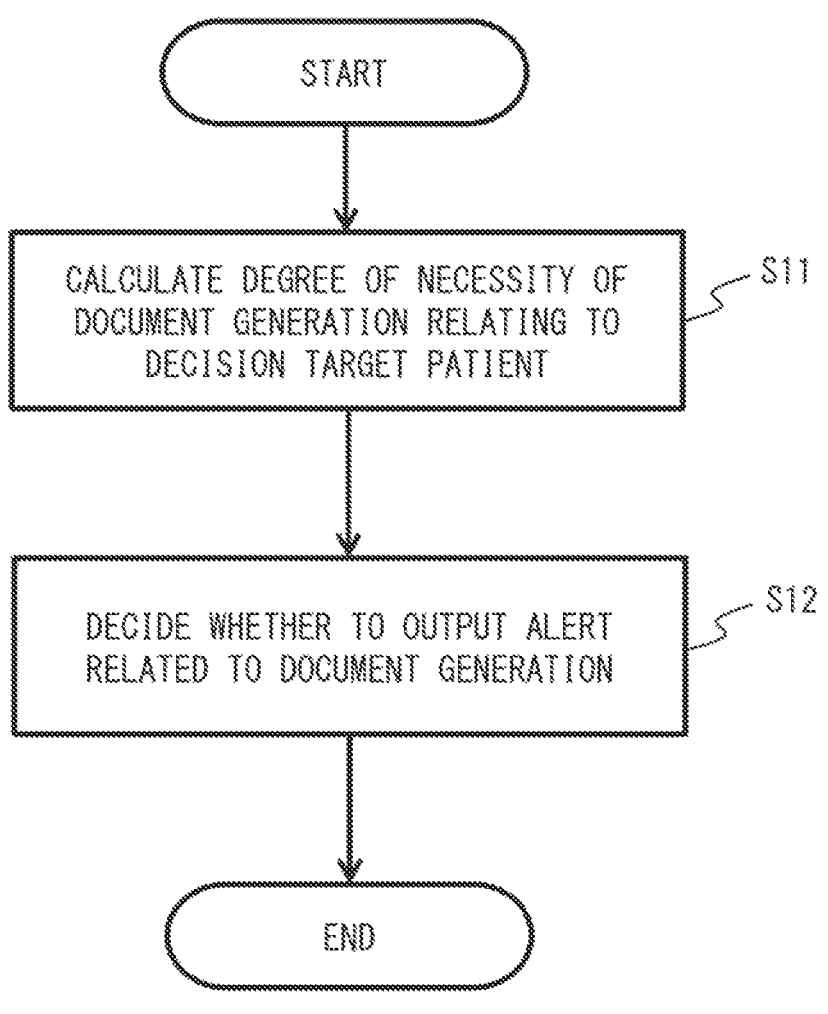
FIG. 2 is a flowchart illustrating one example of processing executed by the decision apparatus according to the disclosure.

FIG. 2 is a flowchart illustrating one example of representative processing of the decision apparatus 10, and the processing of the decision apparatus 10 is described by the flowchart. Note that, details of each piece of processing are as described above, and therefore, description thereof will be omitted.

First, the degree-of-necessity calculation unit 11 of the decision apparatus 10 calculates a degree of necessity of generation of a document relating to a decision target person, by inputting state information of the decision target person with respect to a learning model learned in advance (step S11; calculation step). The alert decision unit 12 decides whether to output an alert related to document generation of the decision target person, by using the degree of necessity calculated by the degree-of-necessity calculation unit 11 and information indicating whether the document has actually been generated for the decision target person (step S12; decision step).

Description of Advantageous Effect

As described above, the decision apparatus 10 can issue an alert to a user when, for example, the degree of necessity calculated by the degree-of-necessity calculation unit 11 is a predetermined value and document generation of the decision target person is not performed. The alert prompts to appropriately perform document generation relating to the decision target person. The alert allows a user to notice that document generation relating to the decision target person is necessary, and to take an action such as performing document generation. Therefore, it is possible to suppress a risk such as return of a medical treatment fee, administrative disposition, and litigation caused by neglect of a necessary document without being generated.

(1B)

Next, in (1B), a learning apparatus capable of generating a learning model will be described.

[Description of Configuration]

Figure 3:
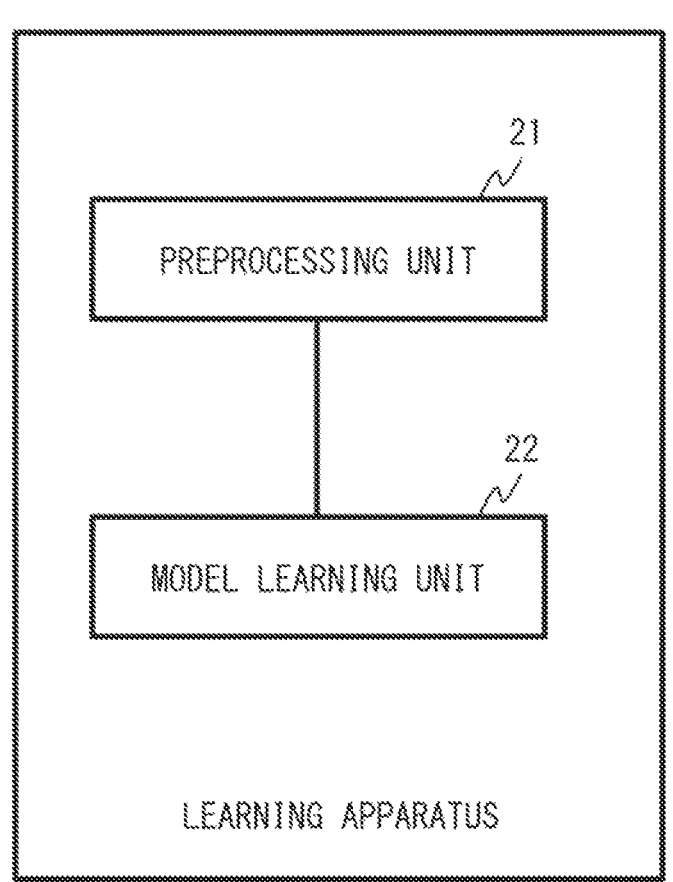
FIG. 3 is a block diagram illustrating one example of a learning apparatus according to the disclosure.

FIG. 3 is a block diagram illustrating one example of a learning apparatus. A learning apparatus 20 includes a preprocessing unit 21 and a model learning unit 22. Each unit (each means) of the learning apparatus 20 is controlled by a not-illustrated control unit (controller). Hereinafter, each unit will be described.

The preprocessing unit 21 generates state information of a person by performing preprocessing on data related to a state of the person. The preprocessing is processing of performing in order to convert data into a format suitable for input to a learning model. The data being subject to the preprocessing may include at least any of pieces of structured data or unstructured data. When the unstructured data are included in the data, the preprocessing unit 21 can perform preprocessing by any of bag of words (BoW), Word2Vec, and bidirectional encoder representations from transformers (Bert), for example. The data relating to the state of the person and the state information of the person include any piece of information of one or a plurality of types directly or indirectly indicating a physical state of the person. Details of the definition are as described in (1A), and thus description thereof will be omitted.

The model learning unit 22 learns a learning model by using learning data including state information of a person generated by the preprocessing unit 21 and information indicating whether generation of a document relating to the person is necessary or unnecessary. Details of the definition of a document relating to a person are as described in (1A), and thus description thereof will be omitted. Any technique such as logistic regression, an SVM, or a neural network can be used for learning the learning model.

The learning data include the above-described state information and information indicating whether document generation is necessary or unnecessary for a person to be learned. Therefore, the learning model learns, by using the learning data, whether a degree of necessity of document generation is high (or low) when a person is in what state. After the learning model is learned, when the state information of a decision target person is input to the learning model as an explanatory variable, a degree of necessity of generation of a document relating to the decision target person is calculated as an objective variable, and is output. An example of the degree of necessity to be calculated is as described in (1A).

[Description of Processing]

Figure 4:
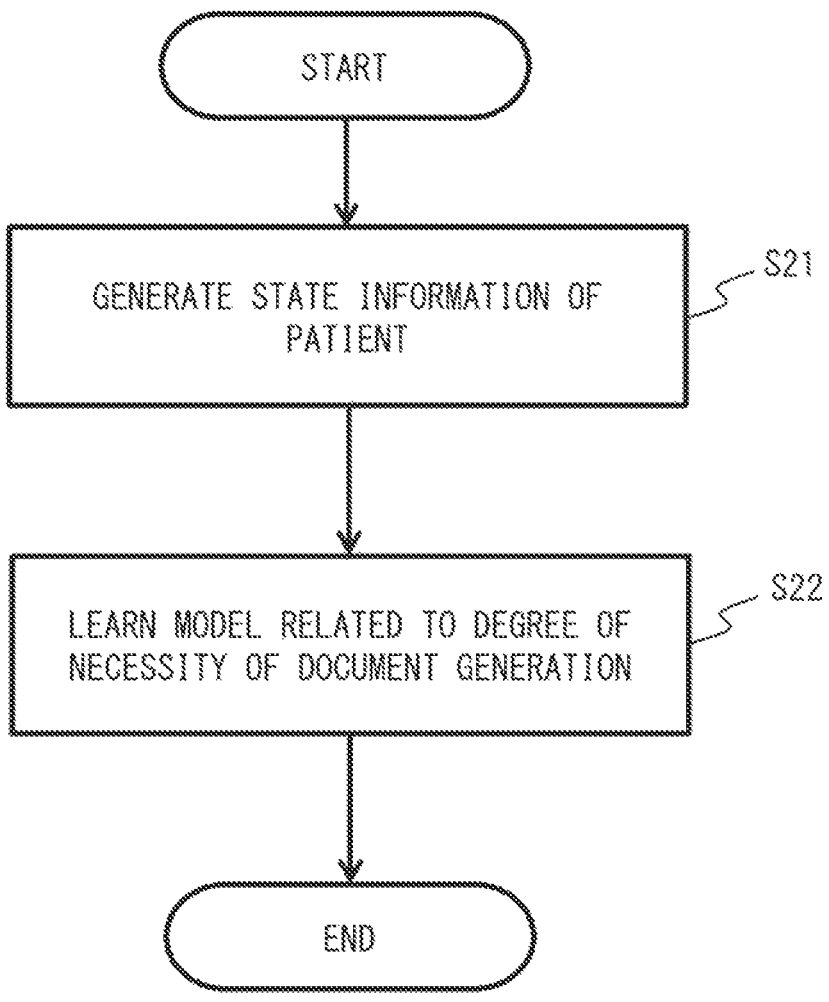
FIG. 4 is a flowchart illustrating one example of processing executed by the learning apparatus according to the disclosure.

FIG. 4 is a flowchart illustrating one example of representative processing of the learning apparatus 20, and the processing of the learning apparatus 20 is described by the flowchart. Note that, details of each piece of processing are as described above, and therefore, description thereof will be omitted.

First, the preprocessing unit 21 of the learning apparatus 20 performs preprocessing on data related to a state of a person, and thereby generates state information of the person (step S21; generation step). The model learning unit 22 learns a model calculating a degree of necessity of generation of a document relating to a decision target person, by using learning data including the state information of the person and information indicating whether generation of a document relating to the person is necessary or unnecessary (step S22; learning step).

Description of Advantageous Effect

As described above, the learning apparatus 20 can generate learning data for causing a model to learn, and learn a learning model for a decision target person by using the generated learning data. Therefore, by using the learning model, it is possible to prompt to appropriately perform on document generation relating to the decision target person, for example, as described in (1A). Thus, it is possible to make a user to notice that document generation relating to the decision target person is necessary.

Note that, the learning apparatus 20 is connected to the decision apparatus 10 described in (1A), for example, or configures the same apparatus as the decision apparatus 10, so that an artificial intelligence (AI) system for alerting related to document generation can be constructed. A detailed specific example will be described in a second example embodiment.

Second Example Embodiment

Hereinafter, a second example embodiment of the present disclosure will be described with reference to the drawings. In the second example embodiment, a specific example of a system in which the decision apparatus 10 and the learning apparatus 20 described in the first example embodiment are mounted is disclosed. However, a specific example of the apparatus described in the first example embodiment is not limited to the following.

[Description of Configuration]

Figure 5:
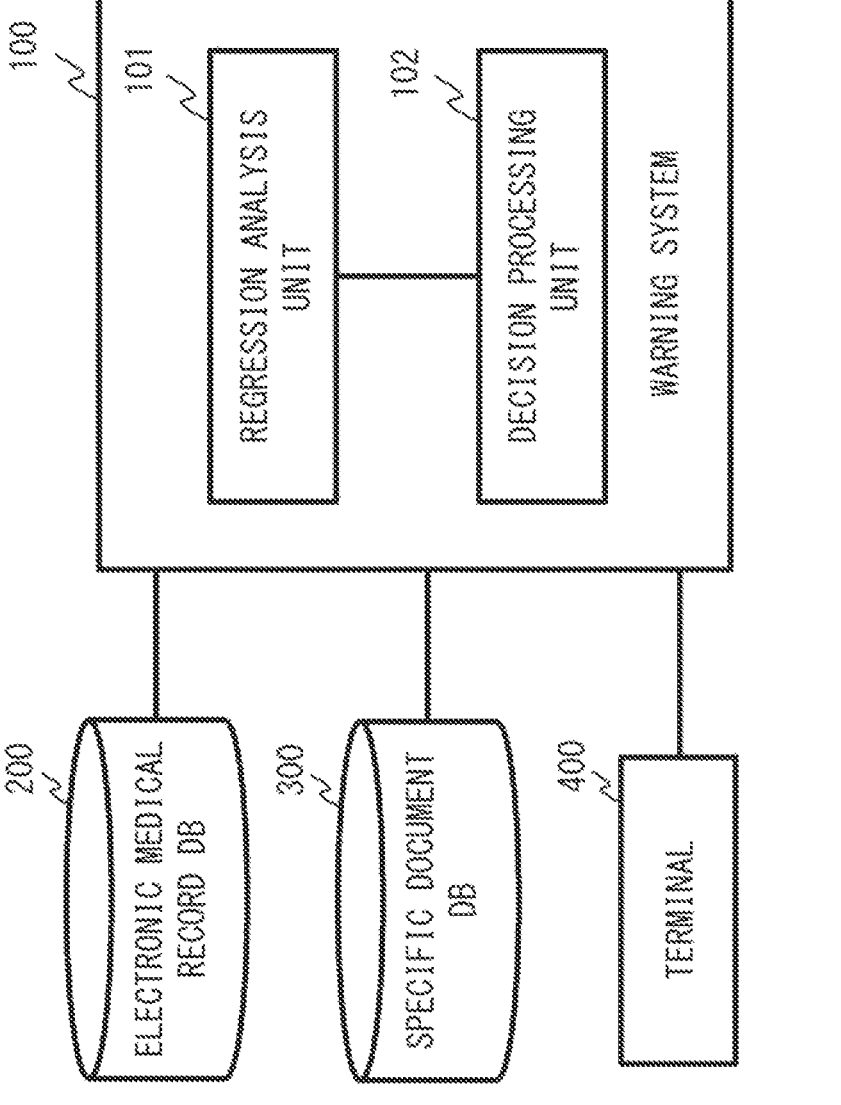
FIG. 5 is a block diagram illustrating one example of a warning system according to the disclosure.

FIG. 5 is a block diagram illustrating one example of a warning system. A warning system 100 is a medical system that manages data of a hospital, and includes a regression analysis unit 101 and a decision processing unit 102. The warning system 100 is communicably connected, via a network, to each of an electronic medical record data base (DB) 200, a specific document DB 300, and a terminal 400.

In the electronic medical record DB 200, information of age, gender, a disease name, a vital sign, an examination result, and a nursing record of a patient, and another document indicating a state of the patient is stored, for each patient, in association with information (for example, a name and a number of the patient and a nurse in charge of the patient) specifying the patient and the nurse in charge thereof, as electronic medical record data relating to the state of the patient. The examination result includes an examination value and an image of medical imaging. The another document includes, but is not limited to, a hospitalization treatment plan and a plan for going-out/staying-away. The nursing record and the another document are recorded as natural language. In addition, the electronic medical record data may also include information, such as sound information, having a property being mentioned as state information of a person in the first example embodiment. The electronic medical record data are updated every time a medical professional such as a nurse newly inputs state information of each patient. Note that, the image in the electronic medical record data can be acquired by being connected to, for example, a camera installed in a medical institution.

The specific document DB 300 stores, for each patient, information relating to a generation history of a specific document being subject for which a degree of necessity of generation is to be decided. The specific document to be decided is one or more documents related to medical care or nursing, and for example, at least any of a document related to a hospitalization treatment plan (as one example, a "hospitalization treatment plan"), a document related to a hospital infection prevention measure (as one example, a "hospital infection prevention measure document"), a document related to a medical safety management system (as one example, a "medical safety management system document"), a document related to a bedsore plan (as one example, a "bedsore plan"), or a document related to a nutritional management system (as one example, a "nutritional management plan"). However, a type of the document is not limited thereto as long as it is a document related to medical care or nursing. As information of the generation history, at least information indicating whether a specific document has been generated is stored. However, the information of the generation history may further include information indicating a generation date when the specific document is generated.

In a learning stage of a first learning model, the warning system 100 acquires the electronic medical record data stored in the electronic medical record DB 200 and history information (information indicating whether generation of a specific document is necessary) indicating presence or absence of specific document generation stored in the specific document DB 300. Then, the first learning model is learned by using the acquired ones as first learning data. Thereafter, the warning system 100 periodically acquires electronic medical record data related to a decision target patient (e.g., a new patient) from the electronic medical record DB 200, and decides whether to output an alert related to specific document generation of the decision target patient, by using the acquired electronic medical record data and the learned first learning model.

When it is decided that an alert is necessary to be output related to generation of a specific document of a certain decision target patient, the alert system 100 outputs an alert to the terminal 400. Details of the processing will be described later. Note that, the above-described series of pieces of processing of acquiring electronic medical record data of a decision target patient, deciding whether to output an alert, and outputting the alert may be executed by the warning system 100 periodically (e.g., with a frequency of once a day or once a week) or irregularly.

The terminal 400 includes a screen and an input unit (e.g., a keyboard or a mouse), and when an alert is output from the warning system 100, the terminal 400 displays the alert on the screen. By looking at the terminal 400, a medical professional can recognize that a specific document of the patient has not been generated, and generate the document by operating the input unit of the terminal 400.

Hereinafter, a detailed configuration of the warning system 100 will be described. As illustrated in FIG. 5, the warning system 100 includes the regression analysis unit 101 and the decision processing unit 102. The regression analysis unit 101 uses electronic medical record data of a plurality of patients and history information of specific document generation for each of the patients, and thereby causes the first learning model to learn in advance whether a degree of necessity of specific document generation is high (or low) when the patient is in what state. Then, by using the first learning model, the regression analysis unit 101 executes inference processing of deciding the degree of necessity of document generation for the decision target patient. The decision processing unit 102 decides whether new generation of a specific document for the decision target patient is necessary, by using the degree of necessity calculated by the regression analysis unit 101, and outputs an alert to the terminal 400 when necessary.

Figure 6:
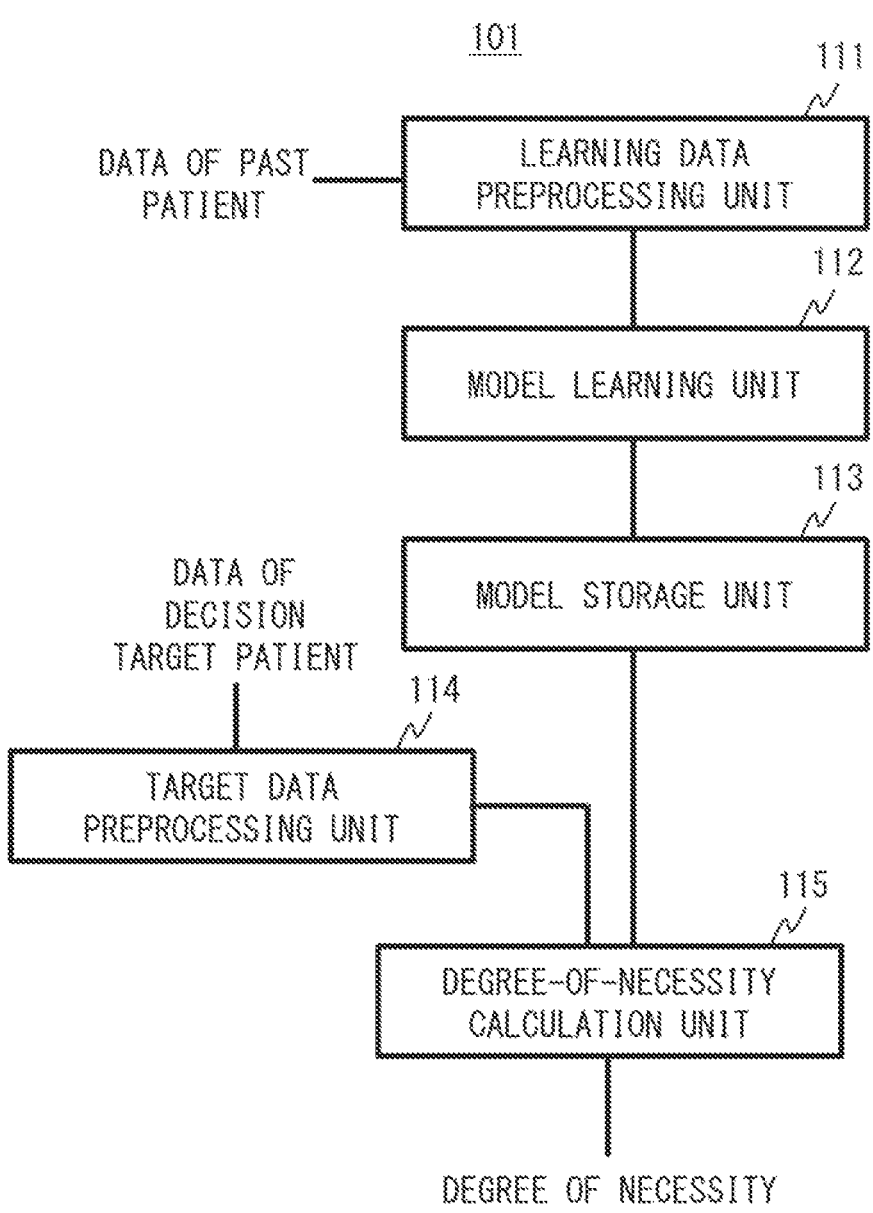
FIG. 6 is a block diagram illustrating one example of a regression analysis unit according to the disclosure.

FIG. 6 is a block diagram illustrating one example of the regression analysis unit 101. The regression analysis unit 101 includes a learning data preprocessing unit 111, a model learning unit 112, a model storage unit 113, a target data preprocessing unit 114, and a degree-of-necessity calculation unit 115. Hereinafter, each unit will be described.

The learning data preprocessing unit 111 acquires electronic medical record data of a patient in past (hereinafter, also referred to as a past patient) as an explanatory variable of the first learning data from the electronic medical record DB 200, and executes preprocessing on the acquired data. As described above, the electronic medical record data include structured data and unstructured data (information such as a document such as a nursing record, an image, and a sound), and the learning data preprocessing unit 111 performs preprocessing in such a way that each item of the pieces of data has a format suitable for being input to the first learning model. For example, the learning data preprocessing unit 111 can execute preprocessing on the unstructured data by a method such as BoW, Word2Vec, or Bert, and thereby convert the unstructured data into vector information being converted into a numeral. In addition, the learning data preprocessing unit 111 specifies a decision target period (time interval) in which presence or absence of document generation is decided for a decision target patient, and extracts electronic medical record data of a past patient for each period. Thus, the learning data preprocessing unit 111 can generate first learning data by extracting a sample set of (past patient, decision target period) of the electronic medical record data.

Further, the learning data preprocessing unit 111 acquires, from the specific document DB 300, history information of specific document generation associated to each sample set of the electronic medical record data of the past patient. For example, when status information of a specific patient at a specific date is included in a certain sample set of electronic medical record data, the learning data preprocessing unit 111 acquires a history of specific document generation of the specific patient at the specific date from the specific document DB 300. Then, the learning data preprocessing unit 111 generates the first learning data by associating a sample set of the extracted history information with the sample set of the electronic medical record data.

FIG. 7 is a table illustrating one example of the first learning data generated by the learning data preprocessing unit 111. In this example, the decision target period in which presence or absence of document generation is decided for a decision target patient is one day, and each sample set of (past patient, days) is extracted with respect to the electronic medical record data and the history information of specific document generation. However, the decision target period in which presence or absence of document generation is decided for a decision target patient is not limited thereto. For example, when the decision target period is one week, each sample set of (past patient, week) is extracted with respect to the electronic medical record data and the history information of specific document generation.

In FIG. 7, a patient A and a patient B are set as samples of the past patient, and a first day and a second day are set as samples of the days, but the number of patients and the days included in the electronic medical record data to be acquired are not limited to this example. In addition, although FIG. 7 illustrates a body temperature, age, and a nursing record converted into vector information as status information (information of electronic medical record data) of a patient in each sample set, information included as status information of a patient is not limited thereto.

In FIG. 7, as history information of generation of a document 1 and a document 2 which are specific documents, information indicating presence or absence of generation is illustrated for the first and second days of the patient A and the first and second days of the patient B. When the history information is "1", it is meant that generation is made, and when the history information is "0", it is meant that generation is not made. The state information of the patient is an explanatory variable in the first learning data, and the history information is information indicating necessity of specific document generation, and is an objective variable in the first learning data. The learning data preprocessing unit 111 outputs the first learning data generated in this way to the model learning unit 112.

The model learning unit 112 executes learning of a model parameter in the first learning model by using the first learning data generated by the learning data preprocessing unit 111. For the first learning model, for example, any technique of logistic regression, an SVM, and a neural network can be used. The first learning model learns, with the learning, whether a degree of necessity of document generation is high (or low) when a patient is in what state. The learned first learning model is stored in the model storage unit 113. Specifically, a model parameter of the learned first learning model is stored in the model storage unit 113.

The target data preprocessing unit 114 acquires electronic medical record data of a decision target patient from the electronic medical record DB 200, and executes preprocessing on the data. The electronic medical record data includes the structured data and the unstructured data described above, and the target data preprocessing unit 114 performs similar preprocessing as the learning data preprocessing unit 111. The details of the preprocessing are as described for the learning data preprocessing unit 111. At this time, the target data preprocessing unit 114 extracts the electronic medical record data associated to the decision target period to be decided with respect to the decision target patient. For example, when the decision target period in which presence or absence of document generation is decided for the decision target patient is one day, the target data preprocessing unit 114 extracts electronic medical record data in the decision target patient on the decision target day. Alternatively, when the decision target period in which presence or absence of document generation is decided for the decision target patient is one week, the target data preprocessing unit 114 can extract electronic medical record data in the decision target patient for one week including the decision target day. The target data preprocessing unit 114 outputs, to the degree-of-necessity calculation unit 115, the electronic medical record data acquired in this way, which has been preprocessed.

The degree-of-necessity calculation unit 115 inputs the preprocessed data of a decision target patient to the learned first learning model stored in the model storage unit 113 as an explanatory variable. As a result, the first learning model calculates a degree of necessity of generation of a specific document relating to the decision target patient as an objective variable. The degree of necessity calculated herein is a probability indicating that generation of a specific document is necessary, and may take a numerical value of equal to or more than 0 and equal to or less than 1. The closer the degree of necessity is to 1, the more it is necessary to generate a specific document, and the closer the degree of necessity is to 0, the more it is unnecessary to generate a specific document. However, a value that the degree of necessity can take is not limited thereto. In addition, the degree-of-necessity calculation unit 115 may perform logit conversion on the probability calculated by the first learning model, and decide the converted numerical value as the degree of necessity. Note that, when there are a plurality of specific documents to be decided, the first learning model calculates the degree of necessity for each specific document.

Figure 8:
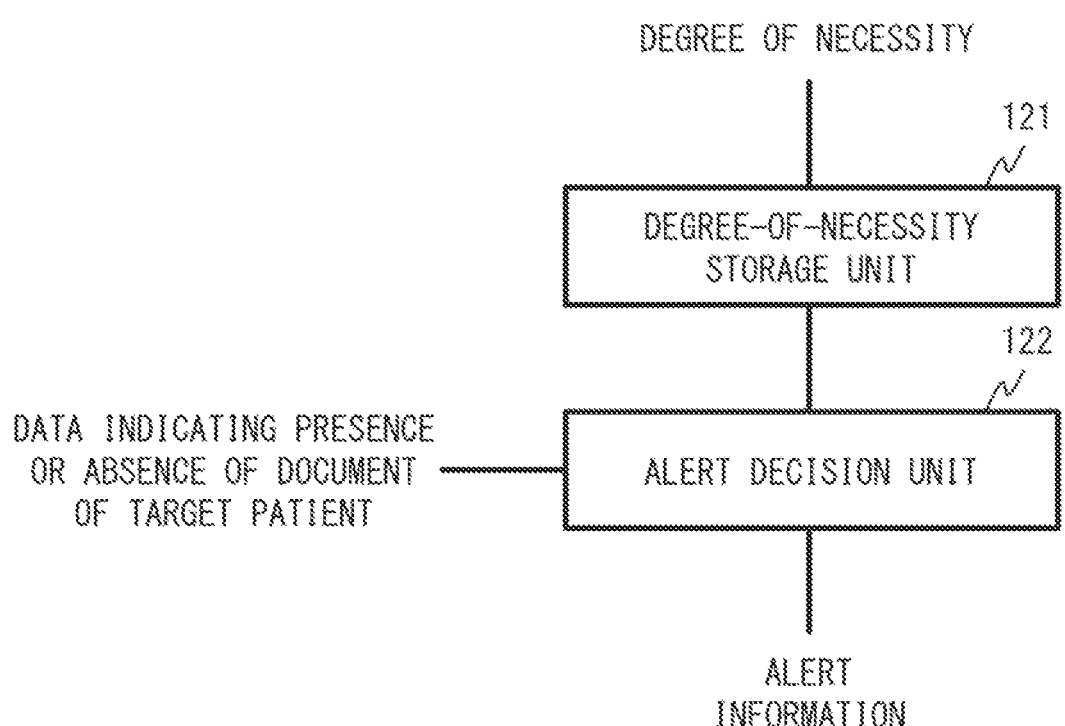
FIG. 8 is a block diagram illustrating one example of a decision processing unit according to the disclosure.

FIG. 8 is a block diagram illustrating one example of the decision processing unit 102. The decision processing unit 102 includes a degree-of-necessity storage unit 121 and an alert decision unit 122. Hereinafter, each unit will be described.

The degree-of-necessity storage unit 121 stores inside a calculation result every time calculation is performed by the degree-of-necessity calculation unit 115, and holds the calculation result as a calculation history. For example, when the decision target period for deciding presence or absence of document generation for a decision target patient is one day, the degree-of-necessity storage unit 121 updates the calculation result of the decision target patient every day, and stores a newly calculated calculation result inside. Note that, the degree-of-necessity storage unit 121 may delete, from the inside, a calculation result after a predetermined period has elapsed from a time of calculation.

Further, the degree-of-necessity storage unit 121 may further store the following threshold value for one or more specific documents to be decided. For example, the degree-of-necessity storage unit 121 may store a predetermined threshold value for deciding necessity of outputting alert information. Alternatively, the degree-of-necessity storage unit 121 may store a predetermined threshold value for deciding whether to change a presentation mode (alert level) of an alert at the terminal 400 when the alert is issued. These threshold values may be the same value for each decision target patient, or may be different values. In addition, these threshold values may be updated as appropriate. Further, these threshold values may be constants, or variables that can be changed according to a condition such as a decision timing (e.g., date).

When the calculation result of the degree of necessity related to the decision target patient stored in the degree-of-necessity storage unit 121 is updated, the alert decision unit 122 decides presence or absence of an alert relating to whether presence or absence of necessity of generation of a specific document.

For example, the alert decision unit 122 acquires, from the degree-of-necessity storage unit 121, a degree of necessity of specific document generation (a degree of necessity of specific document generation at a latest calculation time point by the degree-of-necessity calculation unit 115) that has been updated and newly calculated. In addition, the alert decision unit 122 acquires, from the degree-of-necessity storage unit 121, a predetermined threshold value for deciding necessity of outputting alert information related to the specific document. The alert decision unit 122 compares both, and decides whether the degree of necessity of specific document generation at the latest calculation time point exceeds a predetermined threshold value.

When the degree of necessity of specific document generation at the latest calculation time point does not exceed the predetermined threshold value (when being equal to or less than the predetermined threshold value), the alert decision unit 122 decides that the specific document is not necessary to be generated. On the other hand, when the degree of necessity of specific document generation at the latest calculation time point exceeds the predetermined threshold value, the alert decision unit 122 decides that the specific document is necessary to be generated. At this time, the alert decision unit 122 further accesses the specific document DB 300, and refers to a generation history of the specific document being decided to be necessary to be generated for the decision target patient. Then, it is decided whether the specific document decided to be necessary to be generated has already been generated for the decision target patient.

When the specific document decided to be necessary to be generated has already been generated, the alert decision unit 122 decides that issue of an alert related to the specific document of the decision target patient is unnecessary.

However, even in a case where a specific document being decided to be necessary to be generated has already been generated, when a generation date of the specific document is outside the decision target period (i.e., outside a valid period), the alert decision unit 122 can consider that the specific document being decided to be necessary to be generated has not been generated. For example, when the decision target period is one day, while the latest generation date of the specific document is one day before the date on which the degree of necessity is calculated, the alert decision unit 122 can consider that the specific document to be decided is not generated. Similarly, when the decision target period is one week, while the latest generation date of the specific document is more than a week before the date on which the degree of necessity is calculated, the alert decision unit 122 can consider that the specific document to be decided has not been generated.

The alert decision unit 122 decides that a specific document to be generated at a current stage has not been generated (i.e., there is omission of generation) for the decision target patient, when the specific document decided to be necessary to be generated has not been generated or when it is considered that the specific document has not been generated. Therefore, the alert decision unit 122 decides that issue of an alert related to the specific document of the decision target patient is necessary, generates alert information related to the specific document of the decision target patient, and outputs the generated alert information to the terminal 400. The alert information may include information specifying a decision target patient and a nurse in charge of the patient (e.g., at least any of a name or a number in the decision target patient and the nurse in charge of the patient), information specifying a specific document being decided to have omission of generation, and information (expression such as wording) indicating that the generation is required at the current stage. Further, the alert information may include at least any of a degree of necessity calculated by the degree-of-necessity calculation unit 115 as exceeding a predetermined threshold value, or expression such as a sentence indicating necessity of generation of a specific document, based on the degree of necessity. Note that, the alert decision unit 122 generates alert information by extracting information specifying the decision target patient and the nurse in charge thereof from the electronic medical record data of the decision target patient.

In addition, the alert decision unit 122 can also acquire, from the degree-of-necessity storage unit 121, a past calculation result for a predetermined period from the latest calculation time point for the specific document of the decision target patient. The alert decision unit 122 can predict a degree of necessity of specific document generation in future (for example, future within a predetermined time period from the latest calculation time, such as by a next day or a day after the next day of the latest calculation time), by using the degree of necessity of specific document generation at the latest calculation time point and the acquired calculation result of the degree of necessity of specific document generation in the past time period. The prediction is executed, for example, when the degree of necessity of specific document generation at the latest calculation time point does not exceed a predetermined threshold value by the above-described decision. However, the prediction may be executed even when the degree of necessity of the specific document generation at the latest calculation time point exceeds the predetermined threshold value.

For the decision target patient, the alert decision unit 122 can predict a numerical value of the degree of necessity of the specific document generation in the future by, for example, an extrapolation method by using a numerical value of the degree of necessity of the specific document generation at the latest calculation time point and a numerical value of the degree of necessity of the specific document generation in the acquired past period. However, a prediction method is not limited thereto. For example, the alert decision unit 122 may calculate the degree of necessity of specific document generation in the future by inputting, to a model for prediction, a numerical value of the degree of necessity of specific document generation at the latest calculation time point and in the acquired past period of the decision target patient. The model for prediction can be learned by using, as the first learning data, data relating to transition of the numerical value of the degree of necessity in a past patient in time series.

When the predicted numerical value of the degree of necessity exceeds a predetermined threshold value for deciding necessity of outputting alert information somewhere in a period from the latest calculation time point to the future, the alert decision unit 122 decides that specific document generation of the decision target patient becomes necessary in the future. Then, the alert decision unit 122 generates the alert information related to the specific document of the decision target patient, and outputs the generated alert information to the terminal 400. The alert information may include information specifying a decision target patient and a nurse in charge thereof, information specifying a specific document being decided to be necessary to be generated in the future, and information specifying a timing to be predicted to be necessary to be generated. In addition, the alert information may further include information of a numerical value of the degree of necessity of specific document generation of the decision target patient at the latest calculation time point and in the past period. Further, the alert information may include at least any of a degree of necessity predicted by the alert decision unit 122 exceeding a predetermined threshold value, or expression such as a sentence indicating necessity of generation of a specific document, based on the degree of necessity.

However, the alert decision unit 122 may not generate the alert information and not output the alert information even when it is decided that specific document generation of the decision target patient is necessary in the future, when the specific document decided to be necessary to be generated has already been generated and a predetermined condition is satisfied. The predetermined condition is a case where the generation date of the specific document is within the decision target period (i.e., within a valid period) in view of a future timing at which generation is predicted to be necessary. In this case, the alert decision unit 122 decides that a necessary specific document has been generated at the future timing at which generation is predicted to be necessary, and does not output the alert information. However, when the alert decision unit 122 decides that it is necessary to generate a specific document of the decision target patient in the future without executing this decision, it may uniformly generate alert information related to the specific document of the decision target patient, and output the generated alert information to the terminal 400.

Further, when outputting the alert information, the alert decision unit 122 may change a presentation mode (alert level) at the terminal 400 according to a numerical value of the degree of necessity at the latest calculation time point or the predicted degree of necessity. The alert decision unit 122 decides whether to change a level of the alert by using a predetermined threshold value stored in the degree-of-necessity storage unit 121.

For example, it is assumed that a predetermined threshold value for deciding the degree of necessity is 0.5, and a predetermined threshold value for deciding whether to increase a level of an alert is 0.8, for a certain specific document generation. For a certain specific document generation, when the degree of necessity at the latest calculation time point is 0.7, the degree of necessity at the latest calculation time point exceeds a threshold value related to necessity of issuing an alert, but is equal to or less than a threshold value for decision related to the level of the alert. In this case, the alert decision unit 122 decides that an alert is necessary, but decides that the level of the alert is not necessary to be increased, and outputs the alert having a normal level. On the other hand, when the degree of necessity at the latest calculation time point is 0.9 for a certain specific document generation, the degree of necessity at the latest calculation time point exceeds not only the threshold value related to necessity of issuing an alert but also the threshold value for decision related to the level of the alert. In this case, it is decided that an alert with an increased level is necessary to be issued, and alert information including information on a presentation mode with an increased level is output.

"Increasing a level of an alert" described above means that the terminal 400 is caused to perform a presentation mode in which an appeal of the alert information is increased for a user operating the terminal 400. Specifically, by increasing the level of the alert, it is assumed that a color of the alert information to be displayed on the screen of the terminal 400 becomes more conspicuous, a display area of the alert information is enlarged, the alert information is also notified by sound, volume for notifying the alert information is increased, or the like. Becoming more conspicuous the color of the alert information includes, for example, changing the color displayed for warning from yellow to red, or the like.

In addition, when the level of the alert is increased, the alert decision unit 122 can notify not only the terminal 400 being a target for constantly outputting the alert information but also another predetermined terminal (e.g., a terminal of a person being a supervisor of a document generator, such as a chief nurse). The predetermined terminal is a preset terminal, and the same terminal may be set regardless of the decision target patient and a type of the specific document, or different terminals may be set according to at least any of the decision target patient or the type of the specific document. For example, connection destination information of such a predetermined terminal is stored in the degree-of-necessity storage unit 121. The alert decision unit 122 refers to the connection destination information according to information of the decision target patient and the specific document, thereby specifies a terminal that outputs the alert information other than the terminal 400, and outputs the alert information to the terminal. However, specific change in the presentation mode associated with increasing the level of the alert is not limited to those described above.

The level of the alert is not limited to the two levels of high and low described above, and three or more levels may be set. In this case, a plurality of threshold values are stored in the degree-of-necessity storage unit 121 as the threshold value for decision related to the level of the alert.

When there are a plurality of specific documents to be decided, the alert decision unit 122 executes the above-described processing of decision and output of the alert information with respect to each specific document.

The terminal 400 presents the alert information output from the alert decision unit 122 to a user. The terminal 400 presents the alert information to a user in a mode of display on the screen, sound output by a speaker, or the like. The alert information is presented by the terminal 400 for each specific document for which the alert decision unit 122 decides that an alert is necessary.

Figure 9A:
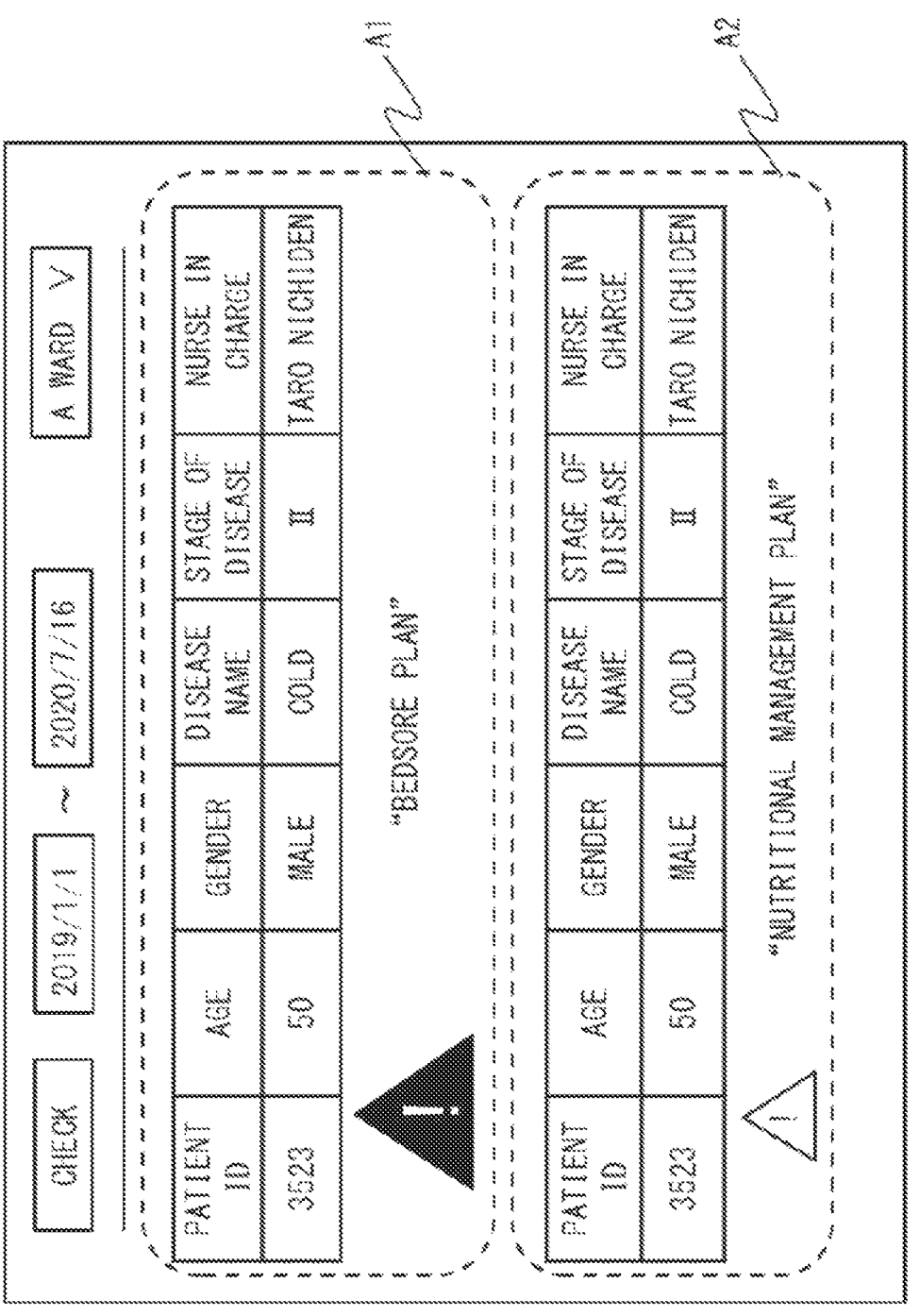
FIG. 9A is a diagram illustrating one example of a terminal display according to the disclosure.

FIG. 9A is a diagram illustrating one example of a terminal display. An image of a graphical user interface (GUI) illustrated in FIG. 9A illustrates a state where alert information A1 and A2 are listed and displayed on a screen when a nurse in charge is displaying the screen of the terminal 400. In the alert information A1, it is displayed that there is omission of generation of a bedsore plan, and in the alert information A2, it is displayed that there is omission of generation of a nutritional management plan. In addition, in the alert information A1 and A2, state information of a patient such as a number (ID) and age of a decision target patient is also displayed on the terminal 400 as information extracted from electronic medical record data. In this way, when the warning system 100 decides that omission of generation of the specific document has occurred, the decision target patient and the corresponding document name can be listed and displayed on the terminal 400.

In FIG. 9A, the level of the alert in the alert information A1 is increased in contrast with the alert information A2. In other words, an exclamation mark indicating an alert is displayed larger with conspicuous color in the alert information A1 as compared with the alert information A2. In addition, the information of the specific document to be alerted is also displayed larger in the alert information A1 as compared with the alert information A2.

The terminal 400 may collate information specifying a nurse in charge and specific information of a nurse in charge included in the alert information when the information specifying the nurse in charge is input at a time of login of a user of the terminal 400 or the like, and present the alert information to the user when the information matches. As another example, in the terminal 400, information associating a nurse in charge with a supervisor thereof may be stored in advance. When information specifying a supervisor of a nurse in charge is input at the time of login of a user or the like, the terminal 400 decides whether the input information specifying the supervisor and the specific information of the nurse in charge included in the alert information match the information stored in advance. When there is a match, the terminal 400 presents the alert information to the user.

In addition, the terminal 400 may be a terminal of a supervisor (e.g., a chief nurse) of a nurse in charge. In this case, the supervisor can collectively grasp and manage the alert information, and when the alert information is output from the alert decision unit 122, the supervisor can transmit the information to the corresponding nurse in charge.

The example in which the alert decision unit 122 outputs alert information to the terminal 400 has been described above. However, the alert decision unit 122 may output the alert information to the electronic medical record DB 200, instead of the terminal 400 or in addition to the terminal 400. In this case, the electronic medical record DB 200 stores the alert information in a state of being associated with the electronic medical record data of the decision target patient or the nurse in charge specified by the alert information.

Figure 9B:
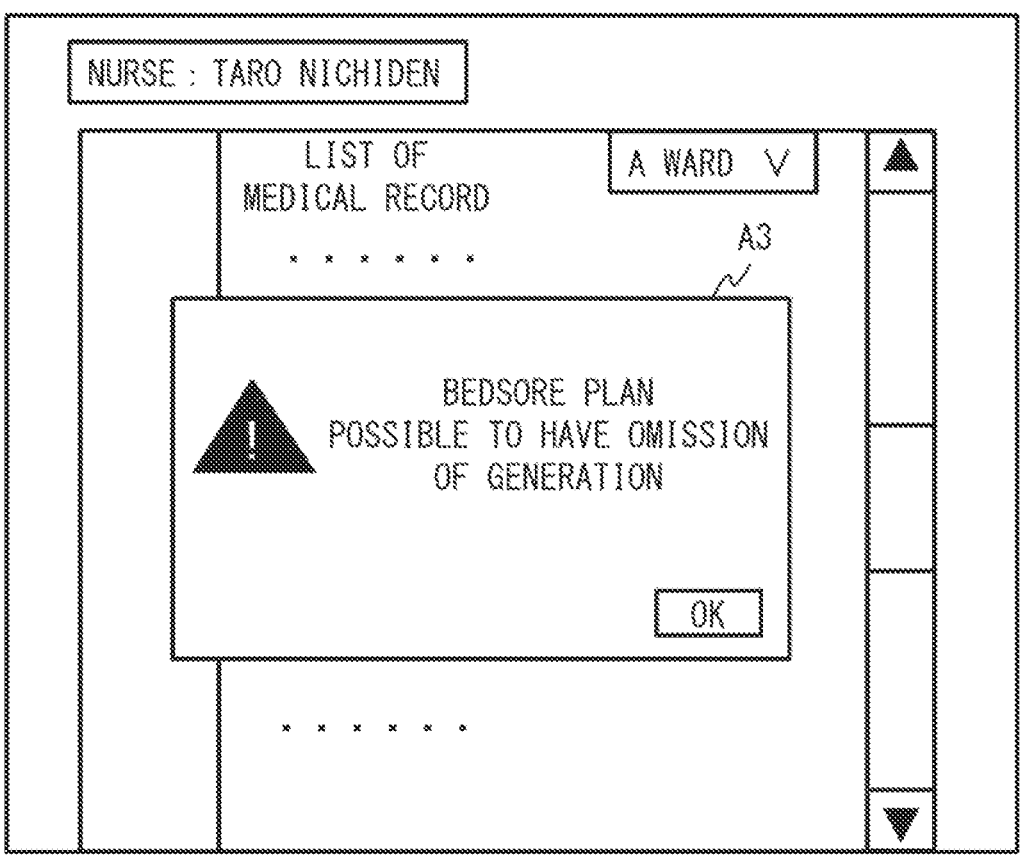
FIG. 9B is a diagram illustrating another example of the terminal display according to the disclosure.

FIG. 9B is a diagram illustrating another example of the terminal display. An image of the GUI illustrated in FIG. 9B indicates a state where a nurse in charge operates the terminal 400, accesses the electronic medical record DB 200, and views electronic medical record data about a decision target patient. It is notified by alert information A3 displayed in a pop-up format that there is omission of generation of a bedsore plan being a specific document for the decision target patient. In this way, it is possible to remind a nurse in charge who performs daily field work that generation of the specific document has been forgotten. However, when not only the nurse in charge but also another nurse or supervisor accesses the electronic medical record DB 200, the terminal 400 can present the alert information in a similar method.

Figure 9C:
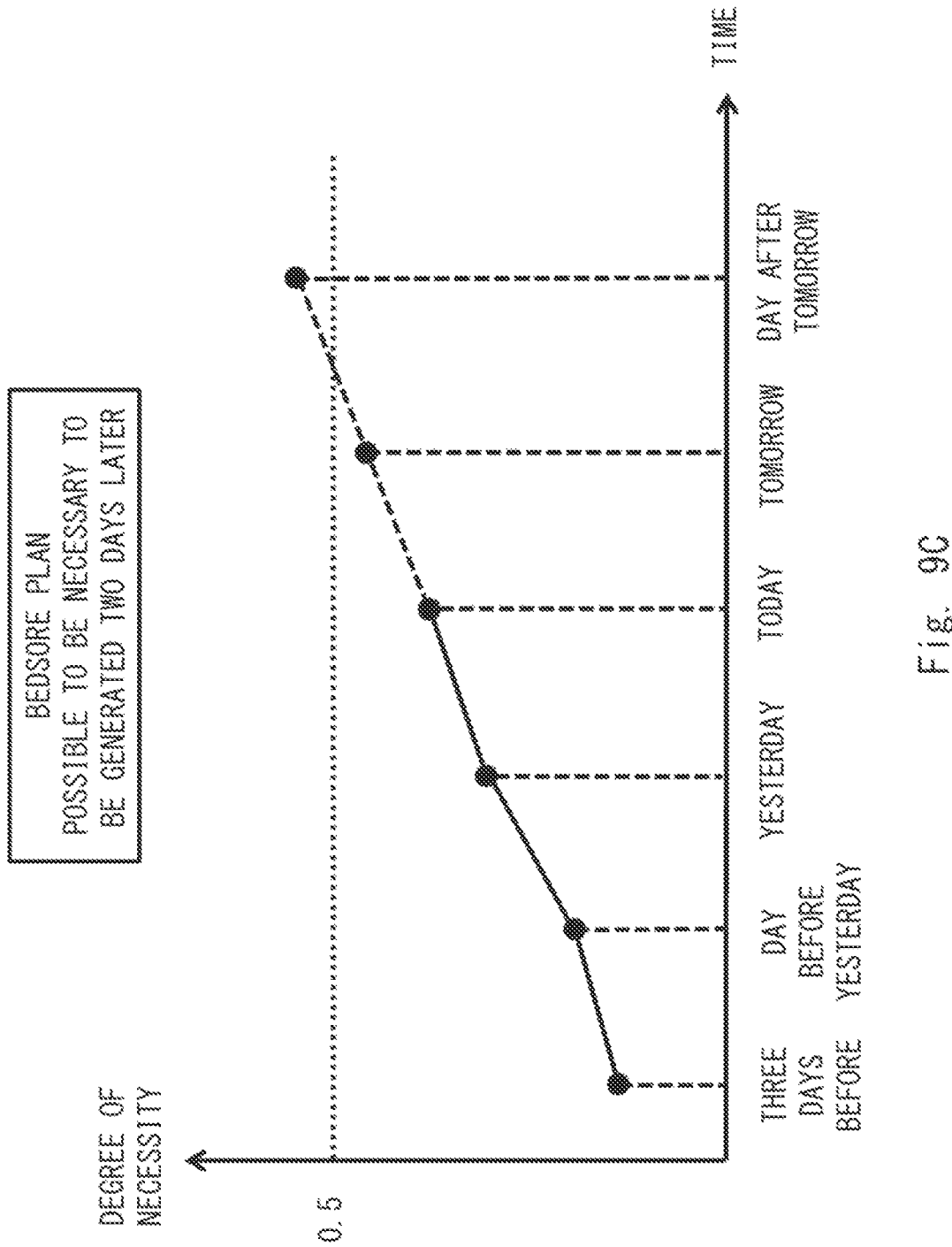
FIG. 9C is a diagram illustrating still another example of the terminal display according to the disclosure.

FIG. 9C is a diagram illustrating still another example of the terminal display. The display indicates alert information when the alert decision unit 122 decides that specific document generation of the decision target patient is necessary in the future two days after the latest calculation time point ("today" in FIG. 9C). The alert information includes information of a specific document decided to be necessary to be generated in the future, information specifying a predicted timing to be necessary to be generated, information of a numerical value of a degree of necessity at the latest calculation time point and in a past period of the decision target patient, and information of a numerical value of a degree of necessity predicted by extrapolation to exceed a predetermined threshold value. The predetermined threshold value is illustrated as 0.5 in FIG. 9C. In addition, although the description is omitted in FIG. 9C, information specifying the decision target patient and the nurse in charge thereof may be further displayed.

[Description of Processing]

Figure 10A:
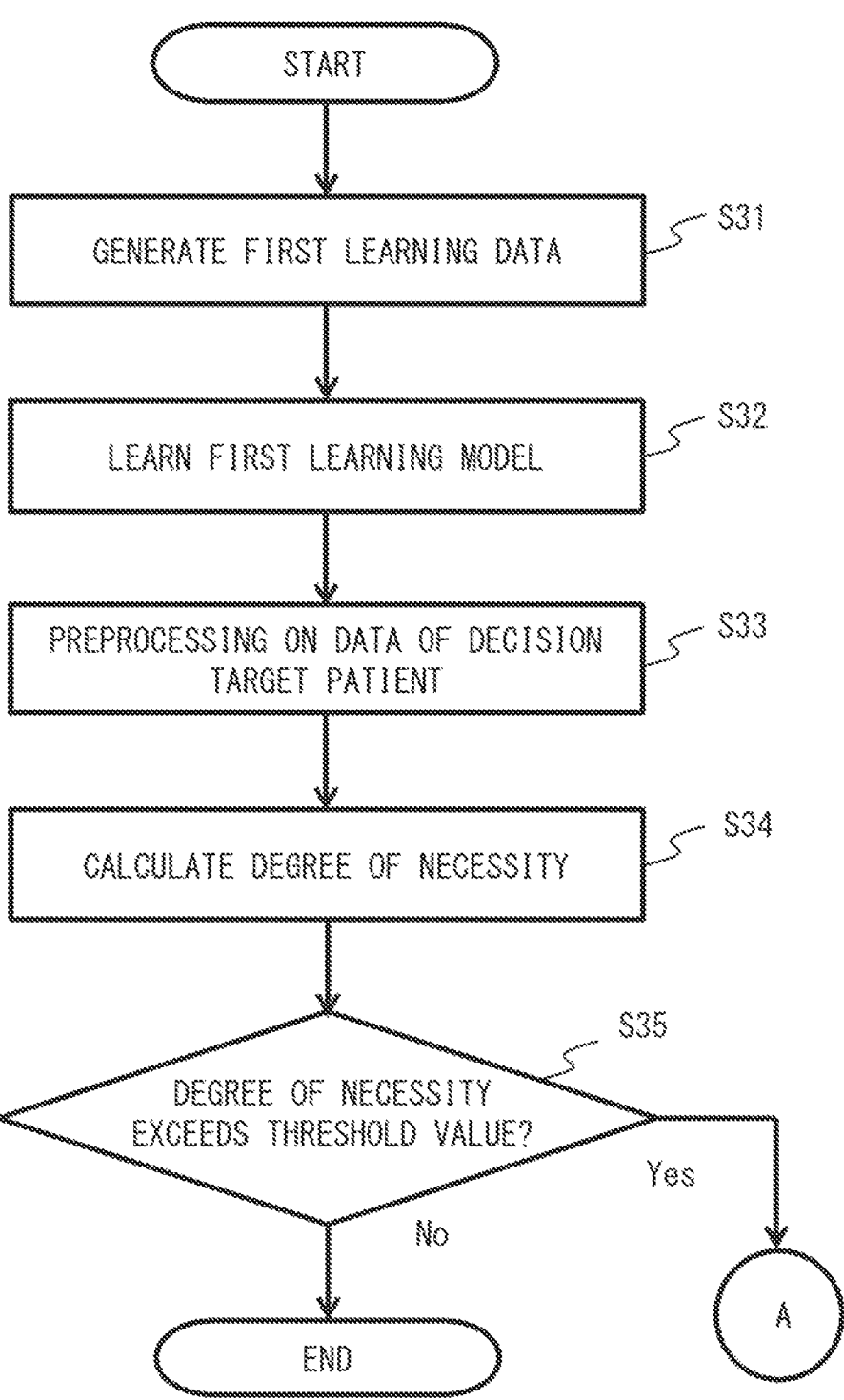
FIG. 10A is a flowchart illustrating one example of processing executed by the warning system according to the disclosure.
Figure 10B:
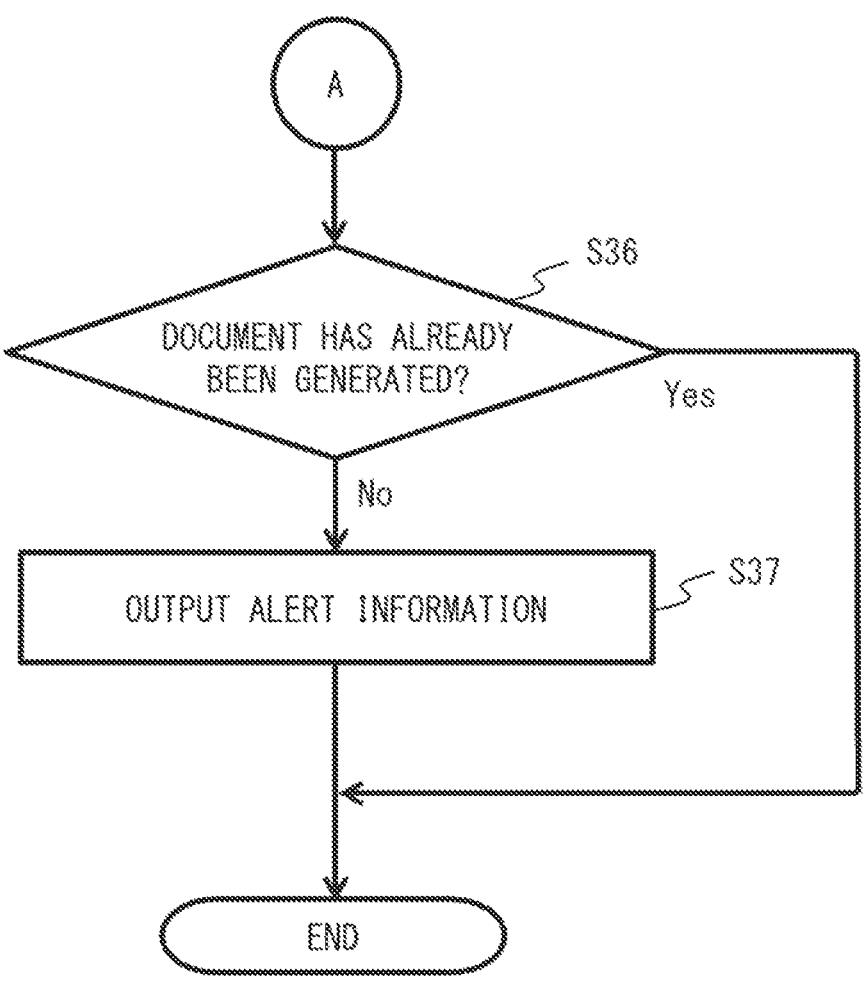
FIG. 10B is a flowchart illustrating one example of processing executed by the warning system according to the disclosure.

FIGS. 10A and 10B are flowcharts illustrating one example of processing executed by the warning system 100, and the processing of the warning system 100 is described by the flowcharts. Note that, details of each piece of processing are as described above, and therefore, description thereof will be omitted.

First, the learning data preprocessing unit 111 acquires electronic medical record data of a past patient from the electronic medical record DB 200, and executes preprocessing on the data. In addition, the learning data preprocessing unit 111 acquires, from the specific document DB 300, history information of specific document generation associated to the electronic medical record data of the past patient. The learning data preprocessing unit 111 generates first learning data, based on the data (step S31). The model learning unit 112 executes learning of a first learning model by using the first learning data generated in step S31 (step S32). Steps S31 to S32 is a learning phase executed before decision processing. The learned first learning model is stored in the model storage unit 113.

The target data preprocessing unit 114 acquires electronic medical record data of a decision target patient from the electronic medical record DB 200, and executes preprocessing on the data (step S33). The degree-of-necessity calculation unit 115 inputs the preprocessed data of the decision target patient to the first learning model, and thereby calculates a degree of necessity of generation of the specific document relating to the decision target patient (step S34). The degree-of-necessity storage unit 121 holds a calculation result by the degree-of-necessity calculation unit 115 as a calculation history.

The alert decision unit 122 compares a numerical value of the degree of necessity related to a predetermined specific document newly stored in the degree-of-necessity storage unit 121 with a predetermined threshold value for decision related to the specific document, and decides whether the degree of necessity exceeds a predetermined threshold value (step S35).

When the degree of necessity does not exceed the predetermined threshold value (No in step S35), the alert decision unit 122 decides that it is not necessary to generate the specific document. In this case, the alert decision unit 122 does not output alert information about the specific document.

On the other hand, when the degree of necessity exceeds the predetermined threshold value (Yes in step S35), the alert decision unit 122 decides that the specific document is necessary to be generated. In this case, the alert decision unit 122 refers to a generation history of the specific document being decided to be necessary to be generated for the decision target patient, and decides whether the specific document has already been generated (step S36).

When the specific document decided to be necessary to be generated has already been generated (Yes in step S36), the alert decision unit 122 decides that issue of an alert related to the specific document of the decision target patient is unnecessary. In this case, the alert decision unit 122 does not output the alert information about the specific document.

On the other hand, when the specific document decided to be necessary to be generated has not been generated (No in step S36), the alert decision unit 122 decides that the specific document to be generated at a current stage has not yet been generated (i.e., there is omission of generation) for the decision target patient. Therefore, the alert decision unit 122 decides that issue of an alert related to the specific document of the decision target patient is necessary, and outputs, to the terminal 400, alert information related to the specific document of the decision target patient (step S37).

Description of Advantageous Effect

Since a medical professional such as a nurse is busy, there is a possibility that document generation to be necessary may be forgotten in a process of taking medical care of a patient. In particular, there is a document for which it is difficult to generate an explicit rule for deciding necessity of document generation. A specific example of such a document includes a bedsore plan or the like. These documents require a professional skill of a medical professional to decide an occurrence risk of bedsore of a patient or a state of a patient such as undernutrition, and therefore, it is difficult to generate the explicit rule for decision. When a medical professional forgets to generate such a document, there are few people who are aware of necessity of the generation, and there is a concern that the generation will be forgotten as it is.

The warning system 100 according to the second example embodiment can solve this problem. Specifically, the warning system 100 utilizes past data as the first learning data, learns a relationship between state information of a patient (including a detection value indicating a physical state and document information such as a nursing record) and necessity of document generation by AI, and thereby generates the first learning model. In addition, the warning system 100 automatically analyzes the state information of a decision target patient by using the first learning model, and outputs an alert by deciding a degree of necessity of document generation, so that it is possible to suppress omission of generation of a necessary document. In short, the warning system 100 functions as a support system for a medical professional.

In addition, any of logistic regression, an SVM, and a neural network may be used for learning of the first learning model. Thus, it is possible to easily execute learning processing of the first learning model by applying an existing algorithm.

In addition, the degree-of-necessity calculation unit 115 may calculate, as a degree of necessity, a probability output by the first learning model or a value acquired by logit-converting the probability, which relates to at least any of necessary or unnecessary of generation of a specific document. Thus, the degree of necessity is represented in an easy-to-understand manner, so that calculation processing required for deciding an alert is reduced, and also a concept of the degree of necessity can be clearly understood when a user refers to the degree of necessity.

In addition, the alert decision unit 122 may output an alert related to specific document generation of the decision target patient when the degree of necessity calculated by the degree-of-necessity calculation unit 115 exceeds a predetermined threshold value and the specific document is not actually generated for the decision target patient. Thus, it is possible to surely give a user a notice and cause a user to generate a document that has not been generated even though it is a specific document being considered to have high necessity to be generated.

In addition, the alert decision unit 122 may predict a future degree of necessity in the decision target patient, based on a degree of necessity at a latest calculation time point calculated by the degree-of-necessity calculation unit 115 and a past degree of necessity calculated in past for the decision target patient. When the predicted degree of necessity exceeds a predetermined threshold value, the alert decision unit 122 outputs an alert related to document generation of the decision target patient. Thus, it is possible to give a user a notice in advance and prevent from forgetting to generate a specific document being considered to have high necessity to be generated in the future.

In addition, the electronic medical record data (state information) of the patient and the electronic medical record data (state information) of the decision target patient used as the first learning data may include structured data and unstructured data being subjected to preprocessing. Thus, even information such as a document such as a nursing record recorded in natural language, an image, and a sound can be used to decide whether a specific document is to be generated, so that decision accuracy can be improved.

In addition, the unstructured data may be preprocessed by a method of any of BoW, Word2Vec, and Bert, and input to the first learning model. Thus, the existing algorithm can be applied, and the preprocessing of the unstructured data can be easily executed.

In addition, the specific document relating to the patient may be at least any of a document related to a hospitalization treatment plan of the patient, a document related to a hospital infection prevention measure of the patient, a document related to a medical safety management system of the patient, a document related to a bedsore plan of the patient, or a document related to a nutritional management system of the patient. Thus, it is possible to improve work of a medical professional in a medical institution such as a hospital.

In addition, the alert decision unit 122 may change a mode of an alert to be presented to a user, based on the degree of necessity calculated by the degree-of-necessity calculation unit 121. Thus, when the degree of necessity of specific document generation is high, an alert that emphasizes the necessity more is possible, so that it is possible to prompt a user such as a nurse to generate a specific document having high necessity.

Note that, the decision processing unit 102 can output, to the terminal 400, the degree of necessity calculated for the decision target person and stored in the degree-of-necessity storage unit 121 even when alert information is not output. For example, when data of the degree of necessity of the decision target patient are updated, at least any of the data of the degree of necessity, the data of the degree of necessity of the decision target patient in the past within a predetermined period from a time of updating, or the data of the degree of necessity predicted for the future within a predetermined period from the time of updating may be output to the terminal 400. Thus, the degree of necessity of specific document generation is visualized to a user, so that it is possible to give some attention to presence or absence of specific document generation in the future and some notice about a state of the decision target patient.

Third Example Embodiment

Hereinafter, a variation of the second example embodiment will be described. Note that, in the following description, description of a same point as that of the warning system 100 according to the second example embodiment will be omitted.

[Description of Configuration]

Figure 11:
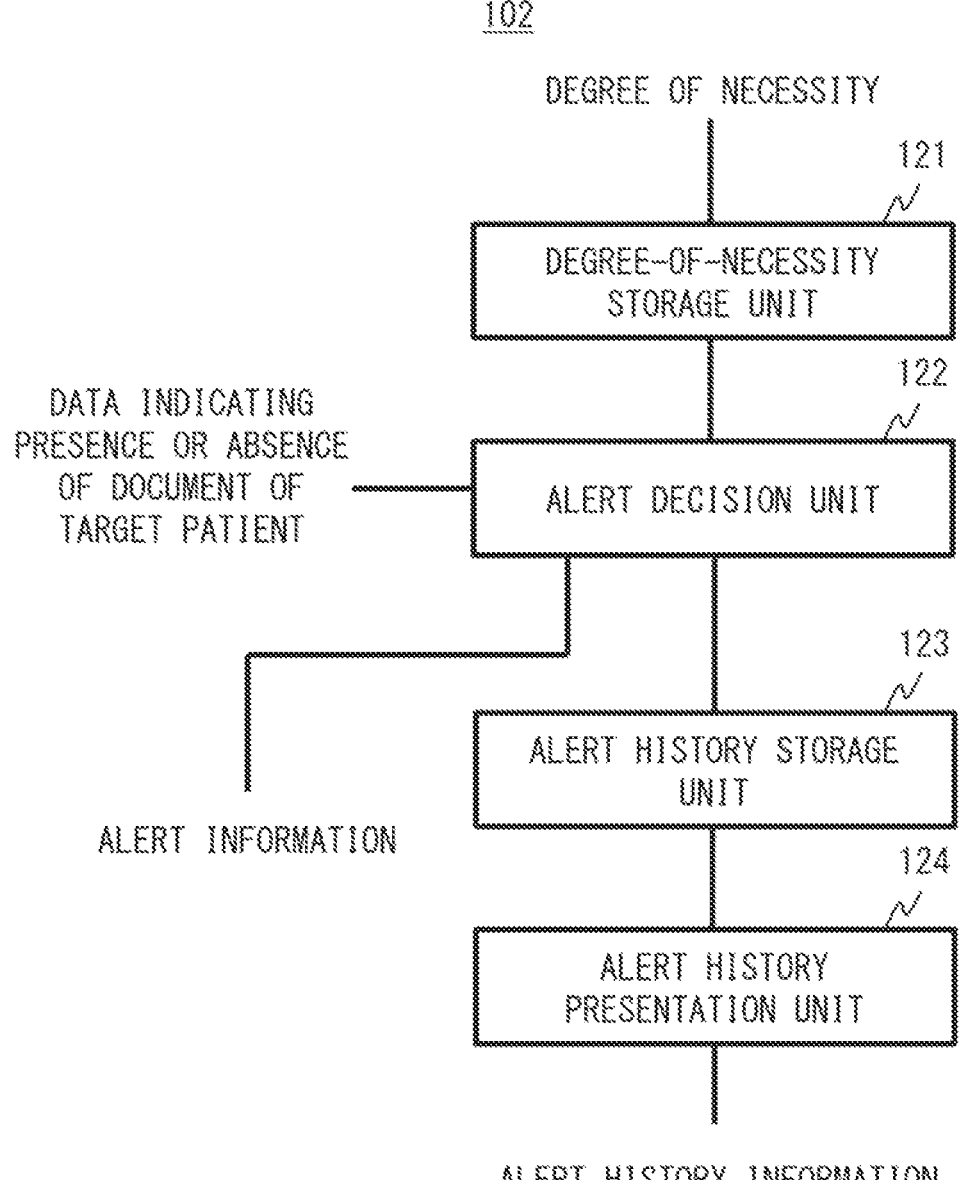
FIG. 11 is a block diagram illustrating one example of a decision processing unit according to the disclosure.

FIG. 11 is a block diagram illustrating one example of a decision processing unit 102. The decision processing unit 102 includes an alert history storage unit 123 and an alert history presentation unit 124 in addition to a degree-of-necessity storage unit 121 and an alert decision unit 122. The degree-of-necessity storage unit 121 and the alert decision unit 122 are the same as those described in the second example embodiment, and thus description thereof will be omitted.

The alert history storage unit 123 stores history information of output alert information when the alert decision unit 122 decides that there is omission of generation of a specific document and outputs the alert information to a terminal 400. The history information to be stored may include, for example, information specifying a decision target patient and a nurse in charge thereof, a degree of necessity calculated by a degree-of-necessity calculation unit 115 to be exceeded a predetermined threshold value, information specifying a specific document decided to have not been generated yet, date and time information at which alert information is output, and the like.

However, even when the alert decision unit 122 decides that specific document generation of the decision target patient is necessary in future and outputs the alert information to the terminal 400, the alert history storage unit 123 may store the history information related to the output alert information. The history information may include, for example, information specifying a decision target patient and a nurse in charge thereof, a degree of necessity calculated by the degree-of-necessity calculation unit 115 to be exceeded a predetermined threshold value in the future, numerical information of a degree of necessity of specific document generation at a latest calculation time point and in a past period of the decision target patient, information specifying a timing to be predicted to be necessary to be generated, information specifying a specific document decided to be necessary to be generated in the future, date and time information at which the alert information is output, and the like.

The alert history presentation unit 124 outputs the history information related to the alert information stored in the alert history storage unit 123 to a terminal such as the terminal 400. For example, the alert history presentation unit 124 outputs, to the terminal in response to an instruction from the terminal, the history information related to the alert information in a case where it is decided that there is omission of generation of the specific document. In addition, similarly, the alert history presentation unit 124 may output, to the terminal, for example, in response to an instruction from the terminal, the history information related to the alert information in a case where it is decided that specific document generation of the decision target patient is necessary in the future.

Description of Advantageous Effect

As described above, in the third example embodiment, it is possible to present, to a user, an output history of an alert related to specific document generation of a decision target patient. Therefore, it is possible to prompt a medical professional and the like to generate a specific document by disseminating information related to at least any of omission of generation of the specific document or a generation schedule of the specific document in future.

In addition, an alert system 100 or another system may also be able to reveal a trend in omission of document generation by analyzing information related to alert information stored in the alert history storage unit 123. The analysis is performed based on, for example, information of an attribute (age, gender, a disease name, and the like) of a patient recorded in electronic medical record data, a nurse in charge, and the like. In this way, it is possible to secondarily utilize the information related to the alert information.

Fourth Example Embodiment

[Description of Configuration]

In this example embodiment, an alert decision unit 122 may decide that there is omission of generation of a specific document, when outputting alert information to a terminal 400, extract information necessary for generation of the specific document decided to have the omission of the generation from electronic medical record data (state information) of a decision target patient, and output the extracted information to the terminal 400. The terminal 400 presents the information on a screen or the like.

For example, the alert decision unit 122 acquires, from a specific document DB 300, an item of information necessary for the specific document decided to have omission of generation. Then, the acquired item and the electronic medical record data of the decision target patient are collated with each other, information of the electronic medical record data matching the item is extracted, and the extracted information is output to the terminal 400. The information output to the terminal 400 is, for example, information such as age, gender, a disease name, and an examination result of the decision target patient, but is not limited thereto.

In addition, the alert decision unit 122 may acquire information, in an electronic format, of a specific document decided to have omission of generation. The information in the electronic format may be stored in a warning system 100, or may be stored in another apparatus such as the specific document DB 300. The alert decision unit 122 extracts information of the electronic medical record data to be described in the electronic format from the electronic medical record data of a decision target patient, based on the information of the electronic format. Then, the information is added to the electronic format, and the data in the electronic format to which the information is added is output to the terminal 400. In this case, a user operating the terminal 400 is presented with an electronic format in a state where a part of a necessary matter has already been entered.

Description of Advantageous Effect

In the warning system 100 described above, when it is necessary to generate a specific document, it is possible to support the generation thereof. In particular, when an electronic format in a state where a part of a necessary matter is already entered is presented to a user operating the terminal 400, an effect of reducing a time required for generating a specific document by the user can be improved. Note that, the warning system 100 can perform similar processing of supporting document generation not only when it is decided that there is omission of generation of a specific document but also when it is decided that specific document generation of a decision target patient is necessary in future. However, when it is decided that specific document generation of a decision target patient is necessary in the future, the alert decision unit 122 may not output an electronic format in a state where a part of a necessary matter has already been entered to the terminal 400. This is because, in a case where it is necessary to generate a specific document of a decision target patient in the future, it is conceivable a case where it is not necessary to immediately present an electronic format for describing a specific document to a user.

Fifth Example Embodiment

In a fifth example embodiment, the disclosure related to the first to fourth example embodiments will be described below. In the following (5A), a minimum component related to the disclosure will be described. In addition, in (5B), a specific example (i.e., a variation of the second example embodiment) in a case where the disclosure is applied to the warning system 100 described in the second example embodiment will be described. Note that, in the description of (5B), description of a same point as that of the warning system 100 according to the second example embodiment will be omitted.

(5A)

[Description of Configuration]

Figure 12:
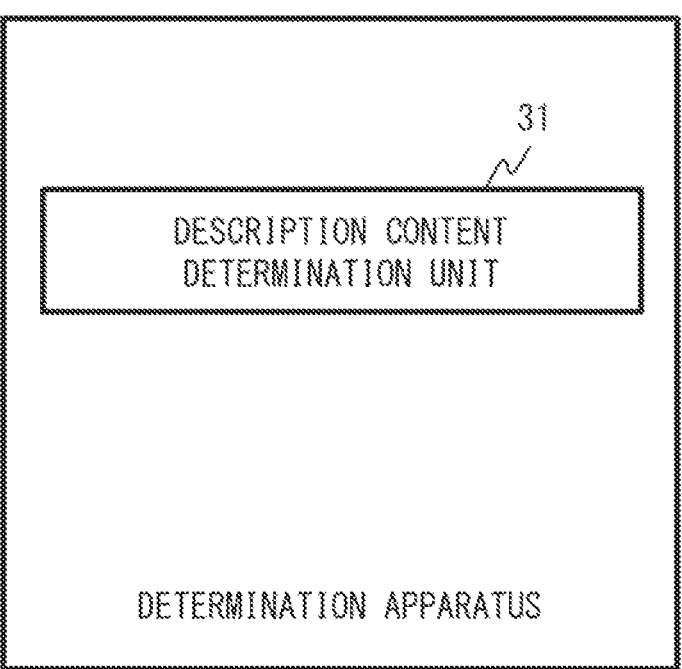
FIG. 12 is a block diagram illustrating one example of a determination apparatus according to the disclosure.

FIG. 12 is a block diagram illustrating one example of a determination apparatus. The determination apparatus 30 includes at least a description content determination unit 31. However, the determination apparatus 30 may further include at least any of a storage unit for storing a learning model for use in inference processing to be described later or an acquisition unit for acquiring state information of an inference target person. Each unit (each means) of the determination apparatus 30 is controlled by a not-illustrated control unit (controller).

The description content determination unit 31 decides, with respect to a predetermined learning model, a description content for each item in a document being necessary to be generated for a person (hereinafter, referred to as an inference target person) to be inferred the description content for each item in the document, by inputting state information of the inference target person. The learning model is a model learned by using learning data including state information of a certain person and a description content for each item in a document generated for the person. Specifically, the learning data are data for machine learning related to a person, include state information of one or more persons as an explanatory variable, and include information indicating a description content for each item in a document generated for the person as an objective variable associated to the explanatory variable. The learning data include a plurality of samples in which an explanatory variable and an objective variable become a set.

A definition of the state information of a person is as described in (1A) of the first example embodiment, and description thereof will be omitted. In addition, since a definition of the document generated for a person is also the same as that of a "document related to a person" described in (1A) of the first example embodiment, the description thereof will be omitted. The learning data include, for a person to be learned, the above-described state information and information indicating a description content for each item in a document generated for the person. Therefore, by using the learning data, the learning model learns what kind of description should be made for each item in the document when a person is in what kind of state. Any technique can be used to generate the learning model, and as one example, any of logistic regression, an SVM, or a neural network can be used. The description content determination unit 31 inputs state information of an inference target person as an explanatory variable to the learned learning model, and thereby derives a description content for each item in a document being necessary to be generated for the inference target person. The state information may be converted into a format suitable for learning before being input to the learning model.

[Description of Processing]

Figure 13:
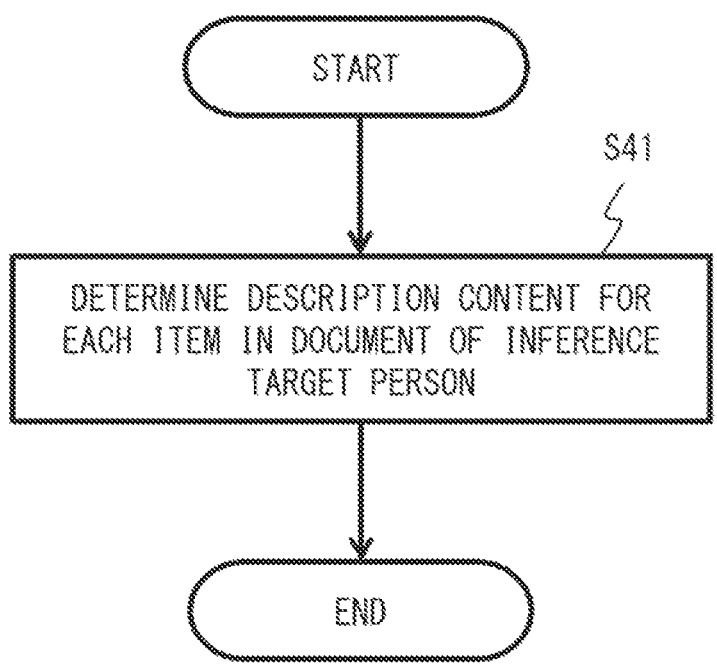
FIG. 13 is a flowchart illustrating one example of processing executed by the determination apparatus according to the disclosure.

FIG. 13 is a flowchart illustrating one example of representative processing of the determination apparatus 30, and the processing of the determination apparatus 30 will be described with the flowchart. Note that, details of each piece of processing are as described above, and therefore, description thereof will be omitted.

The description content determination unit 31 of the determination apparatus 30 inputs state information of an inference target person to a predetermined learning model, and thereby causes to determine a description content for each item in a document to be necessary to be generated with respect to the inference target person (step S41; determination step). The learning model is a model learned by using learning data including state information of a person and a description content for each item in a document generated for the person.

Description of Advantageous Effect

As described above, the determination apparatus 30 can decide a description content for each item in a document being necessary to be generated with respect to an inference target person. Thus, it is possible to prompt a user to give an indication of the description content of the document related to the inference target person and appropriately generate the document. When a user acquires information of the description content, the user can generate a document having an accurate content with respect to the inference target person. Therefore, it is possible to suppress a risk such as return of a medical treatment fee, administrative disposition, and litigation caused by neglect of a necessary document without being generated.

(5B)
[Description of Configuration]

Figure 14:
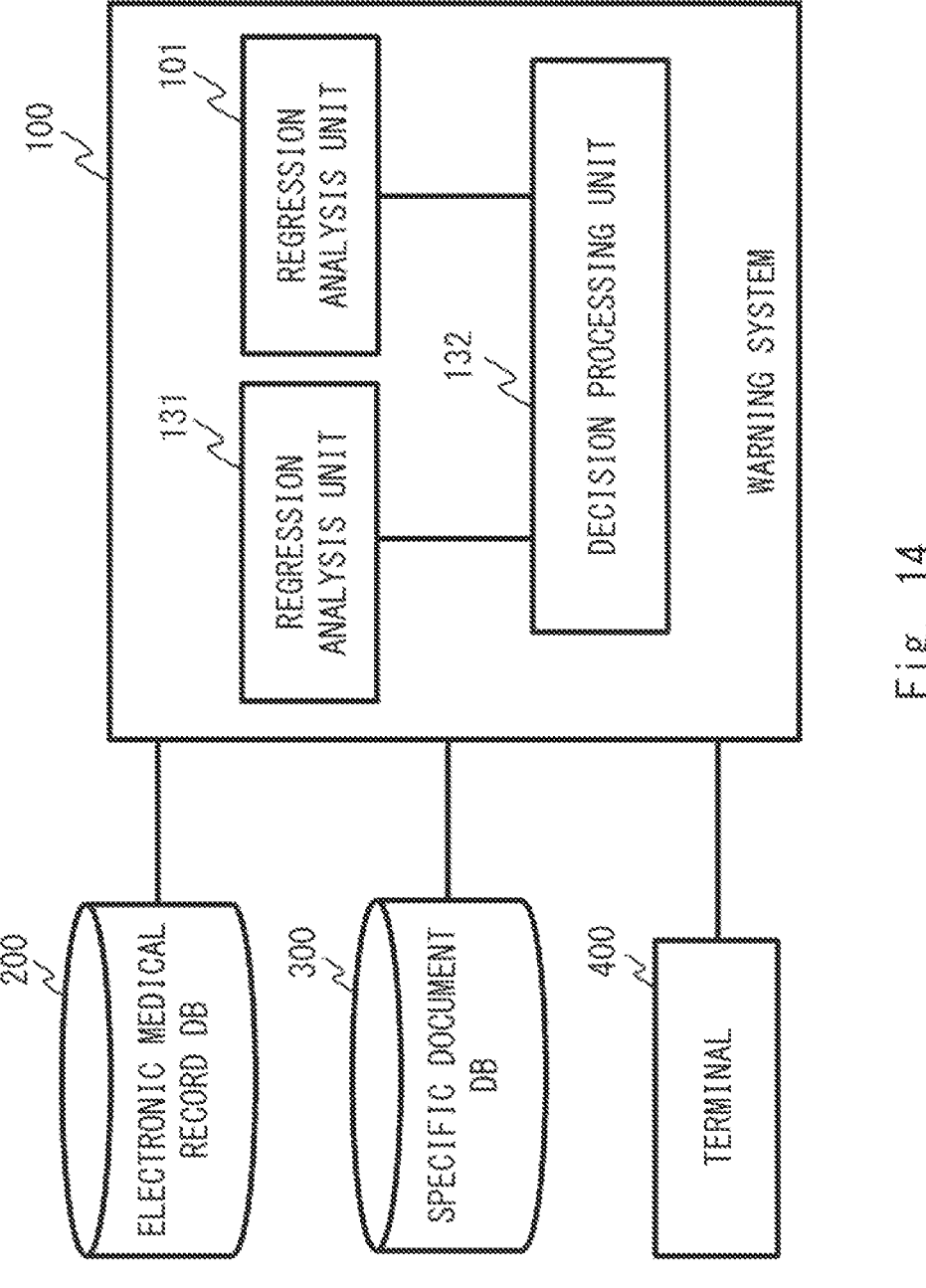
FIG. 14 is a block diagram illustrating one example of a warning system according to the disclosure.

FIG. 14 is a block diagram illustrating one example of a warning system. The warning system 100 is a medical system that manages data of a hospital, and includes regression analysis units 101 and 131, and a decision processing unit 132. The description of the regression analysis unit 101 is the same as that of the second example embodiment, and thus the description thereof is omitted.

Note that, the warning system 100 is communicably connected, via a network, to each of an electronic medical record data base (DB) 200, a specific document DB 300, and a terminal 400. In the specific document DB 300, not only information on a generation history of a specific document (i.e., information indicating a type of a generated document) but also, when the specific document is generated, information of a description content for each item in the specific document is stored for each patient. When the specific document is generated, the specific document DB 300 may further include information indicating the generation date.

Figure 15:
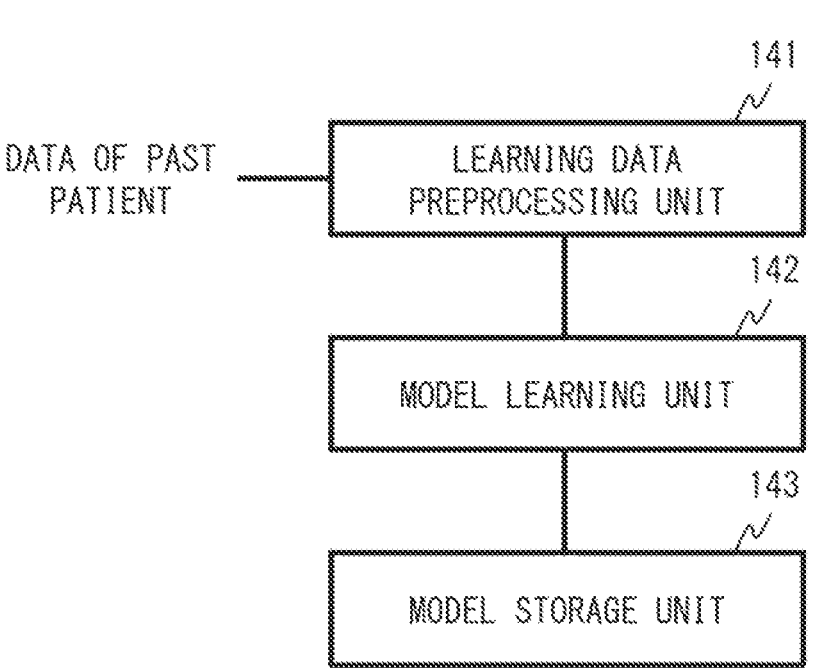
FIG. 15 is a block diagram illustrating one example of a regression analysis unit according to the disclosure.

FIG. 15 is a block diagram illustrating one example of the regression analysis unit 131. The regression analysis unit 131 includes a learning data preprocessing unit 141, a model learning unit 142, and a model storage unit 143. Hereinafter, each unit will be described.

The learning data preprocessing unit 141 acquires electronic medical record data of a past patient as an explanatory variable of second learning data from the electronic medical record DB 200, and executes preprocessing on the acquired data. Processing executed by the learning data preprocessing unit 141 on the electronic medical record data is similar to that executed by the learning data preprocessing unit 111, and thus description thereof is omitted.

Further, the learning data preprocessing unit 141 acquires information indicating a type of a specific document generated for the past patient and information of a description content for each item in the specific document from the specific document DB 300. The specific document is one or more documents related to medical care or nursing as described in the second example embodiment.

FIG. 16 is a table illustrating an example of a description content for each item in a bedsore plan being one example of the specific document. As illustrated in FIG. 16, the description content for each item in the bedsore plan includes information of presence or absence of a bedsore, a site where the bedsore is occurred, a site where the bedsore is likely to occur in the future, a mattress, a measure content taken by a medical professional, use of a medicine that affects occurrence of the bedsore, and the like. The learning data preprocessing unit 141 generates the second learning data by associating a sample set of the information indicating a type of a specific document and the information of such a description content with a sample set of the electronic medical record data.

FIG. 17 is a table illustrating one example of the second learning data generated by the learning data preprocessing unit 141. In this example, a decision target period in which presence or absence of document generation is decided for a decision target patient is one day, and each sample set of (past patient, days) is extracted with respect to the electronic medical record data and history information of specific document generation. However, as described with reference to the description of FIG. 7, the decision target period in which presence of absence of document generation is decided for a decision target patient is not limited thereto.

In FIG. 17, a patient A and a patient B are set as samples of a past patient, and a first day and a second day are set as samples of the days. In addition, FIG. 17 illustrates a body temperature, age, and a nursing record converted into vector information as status information (information of electronic medical record data) of a patient in each sample set. However, these pieces of information are merely examples.

In FIG. 17, as history information of generation of a document 1 being a specific document, information indicating presence or absence of generation is illustrated for the first and second days of the patient A and the first and second days of the patient B. When the history information is "1", it is meant that generation is made, and when the history information is "0", it is meant that generation is not made. Further, in a case where the document 1 is generated, a description content for each item in the document is illustrated as information converted into vector information. Note that, information of a generation history of a plurality of specific documents, such as not only the document 1 but also a document 2, and a description content for each item may be included in the second learning data. State information and a document generation history of a patient are explanatory variables in the second learning data. In addition, the description content for each item of the document is an objective variable in the second learning data. The learning data preprocessing unit 141 outputs the second learning data generated in this way to the model learning unit 142.

Returning to FIG. 15, the description will be continued. The model learning unit 142 executes learning of a model parameter in the second learning model by using the second learning data generated by the learning data preprocessing unit 141. For the second learning model, for example, any technique of logistic regression, an SVM, or a neural network can be used. The second learning model learns, with the learning, what to be described for each item in a document generated for a patient when the patient is in what state. The learned second learning model is stored in the model storage unit 143. Specifically, a model parameter of the learned second learning model is stored in the model storage unit 143.

Figure 18:
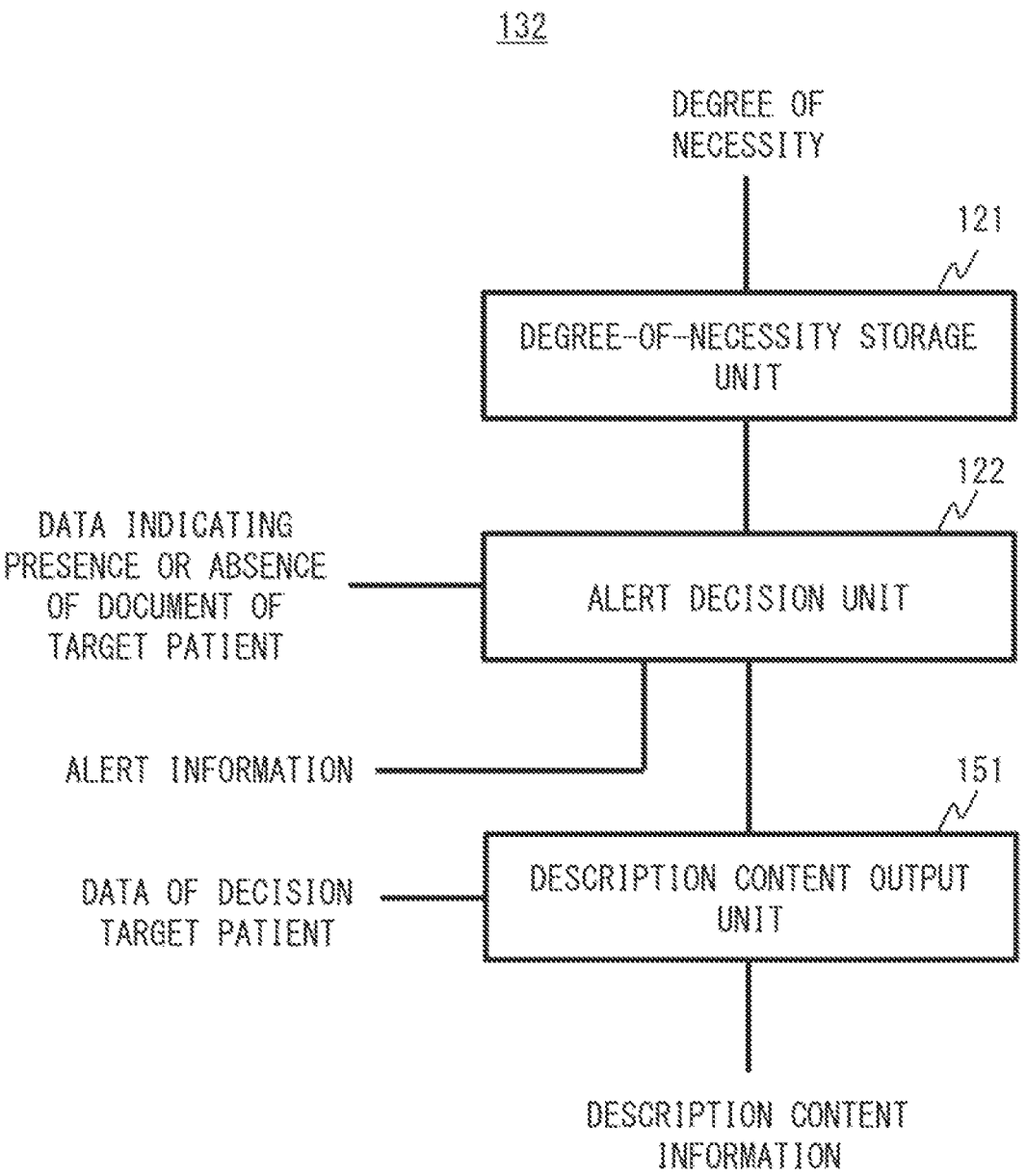
FIG. 18 is a block diagram illustrating one example of a decision processing unit according to the disclosure.

FIG. 18 is a block diagram illustrating one example of the decision processing unit 132. The decision processing unit 132 further includes a description content output unit 151 in addition to a degree-of-necessity storage unit 121 and an alert decision unit 122 included in the decision processing unit 102 according to the second example embodiment. Processing of the degree-of-necessity storage unit 121 and the alert decision unit 122 are the same as those described in the second example embodiment, and therefore, description thereof will be omitted.

When the alert decision unit 122 generates alert information, the generated alert information is output to the description content output unit 151. For example, when a degree of necessity of specific document generation at a latest calculation time point of the degree-of-necessity calculation unit 115 exceeds a predetermined threshold value, the alert decision unit 122 may output the generated alert information to the description content output unit 151. Note that, in a case where it is decided that specific document generation of a decision target patient is necessary in the future, the alert decision unit 122 may or may not output the generated alert information to the description content output unit 151. This is because, in a case where specific document generation of a decision target patient is necessary in the future, it is conceivable a case where it is not necessary to immediately present a description content of a specific document to a user.

When acquiring alert information, the description content output unit 151 recognizes information that is included in the alert information and that specifies a specific document decided to have omission of generation. Then, the description content output unit 151 inputs, as an explanatory variable, the information specifying the specific document in the alert information and data of the decision target patient being preprocessed by the target data preprocessing unit 114, to the learned second learning model stored in the model storage unit 143. As a result, the second learning model calculates, as an objective variable, a description content for each item in a document to be generated for a person of the decision target patient. Note that, in a case where there are a plurality of specific documents decided to have omission of generation in the alert information, the second learning model calculates, as an objective variable, a description content for each item for each of the plurality of specific documents. The description content output unit 151 outputs, to the terminal 400, information of the description content for each item in the specific document being necessary to be generated, which is calculated and output by the second learning model. Note that, the warning system 100 may output the description content to the terminal 400 together with the alert information output from the alert decision unit 122, or may output the description content to the terminal 400 independently of the alert information.

The terminal 400 presents the output information of the description content for each item in the specific document to a user. For example, the terminal 400 displays the description content of the document as illustrated in FIG. 16 on a screen. The terminal 400 can present the description content to a user together with the alert information output from the alert decision unit 122 (for example, it can be simultaneously displayed on a display unit of the terminal 400). However, the terminal 400 may present only the description content to a user.

As another example, the terminal 400 can also present the description content to a user when the user requests after presentation of the alert information. Specifically, as described in the second example embodiment, when the alert information is output from the alert decision unit 122 to the terminal 400, a user operates an input unit of the terminal 400, and thereby indicates to confirm the information. The terminal 400 outputs, to the warning system 100, confirmation information indicating that the user has confirmed the alert information. Based on the confirmation information, the description content output unit 151 outputs information of the description content for each item in the specific document to the terminal 400, and the terminal 400 presents the description content to a user.

[Description of Processing]

Figure 19:
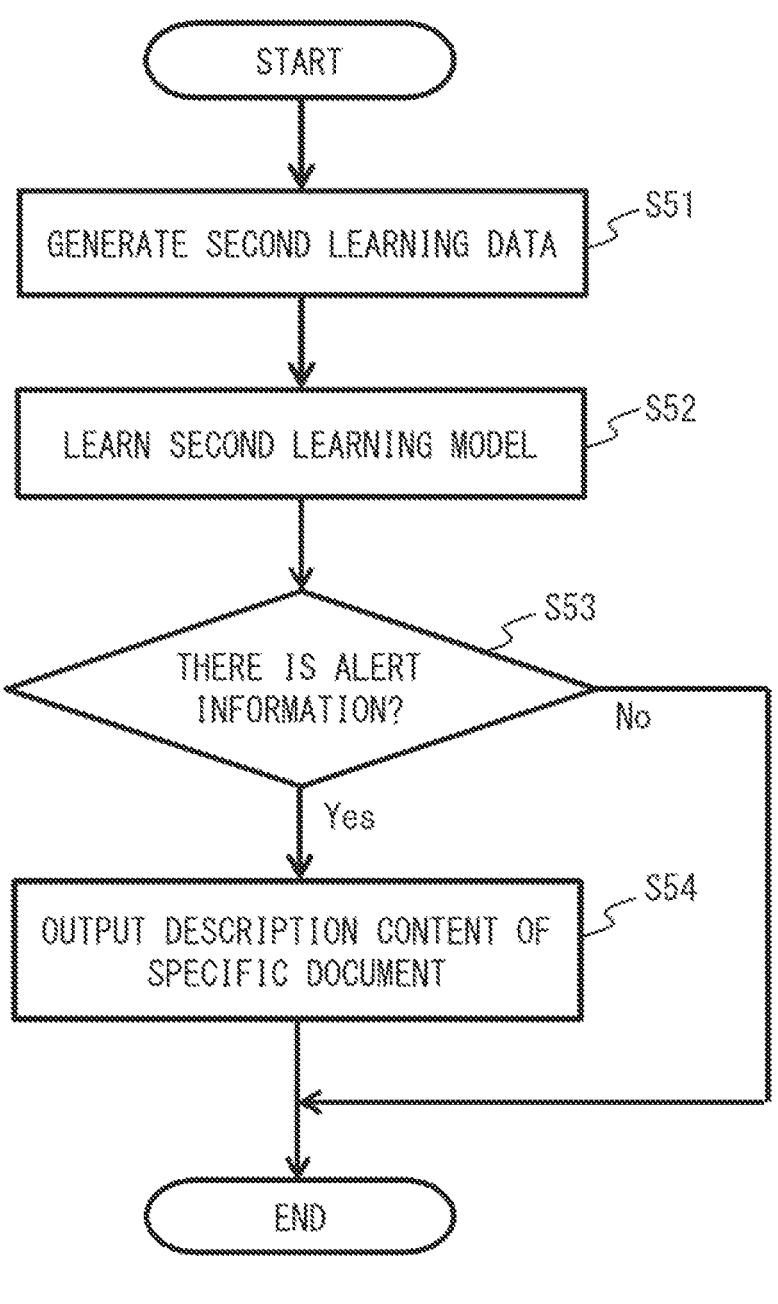
FIG. 19 is a flowchart illustrating one example of processing executed by the warning system according to the disclosure.

FIG. 19 is a flowchart illustrating one example of processing in which the warning system 100 decides a description content of a specific document. Note that, details of each piece of processing are as described above, and therefore, description thereof will be omitted. In addition, the description of the processing illustrated in FIGS. 10A and 10B will be also omitted.

First, the learning data preprocessing unit 141 acquires electronic medical record data of a past patient from the electronic medical record DB 200, and executes preprocessing on the acquired data. In addition, the learning data preprocessing unit 141 acquires, from the specific document DB 300, information indicating a type of a document generated for the past patient and information of a description content for each item in the document. The learning data preprocessing unit 141 generates second learning data, based on the data (step S51). The model learning unit 142 executes learning of a second learning model by using the second learning data generated in step S51 (step S52). Steps S51 to S52 is a learning phase executed before decision processing. The learned second learning model is stored in the model storage unit 143.

The description content output unit 151 decides whether alert information is output from the alert decision unit 122 (step S53). When the alert information is not output (No in step S53), the description content output unit 151 decides that there is no specific document for which the description content is to be determined, and does not execute the processing.

On the other hand, when the alert information is output (Yes in step S53), the description content output unit 151 decides that there is a specific document for which the description content is to be determined. Then, the description content output unit 151 inputs, to the second learning model, information specifying the specific document in the alert information and data of a decision target patient pre-processed by the target data preprocessing unit 114. Thus, the description content for each item in the specific document being necessary to be generated is output. The description content output unit 151 outputs information of the description content for each item in the specific document to the terminal 400 (step S54).

Description of Advantageous Effect

As described above, when alert information is output, the warning system 100 can decide a description content for each item in a specific document being necessary to be generated for a decision target patient, and output the decided description content to the terminal 400. For example, a user being a medical professional can generate a necessary specific document only by confirming or modifying a description content being output from the description content output unit 151. As described above, since a medical professional can generate a specific document with reference to a description content being output by the description content output unit 151, it is possible to simplify document generation work of the medical professional.

Note that, the present disclosure is not limited to the above-described example embodiments, and can be appropriately modified without departing from a scope of the present disclosure. For example, in the second example embodiment, when the alert decision unit 122 decides that a degree of necessity of generation of a specific document exceeds a predetermined threshold value, alert information may be generated and output without deciding whether a specific document decided to be necessary to be generated has already been generated. In addition, a degree of necessity calculated by the degree-of-necessity calculation unit 115 may be information in a qualitative format instead of information such as a numerical value quantitatively expressed. Even in this case, the warning system 100 can execute the decision processing in similar manner to in the second example embodiment.

Those skilled in the art will appreciate that the content of each of the second to fifth example embodiments may be partially achieved, or the content of different example embodiments may be combined as appropriate and achieved. For example, when the fourth and fifth example embodiments are combined, the description content output unit 151 sets in a state where a description content for each item in a specific document is entered in advance in an electronic format for description of the specific document, and outputs, to the terminal 400, the electronic format in which the description content for each item is entered. Thus, it is possible to reduce the number of places for a user to enter in the specific document by himself/herself, and thus it is possible to improve an effect of reducing a time required for generating the specific document.

In the first example embodiment, the decision apparatus or the learning apparatus is not limited to one in which each component is provided in a single apparatus housing, and may have a configuration in which each component is provided in a plurality of housings in a distributed manner. In addition, in the second to fifth example embodiments, the warning system may be provided as a single apparatus, or may be provided as a distributed system in which components are distributed and present among a plurality of apparatuses.

In the example embodiments described above, the present disclosure has been described as a hardware configuration, but the present disclosure is not limited thereto. The present disclosure can also be achieved processing (a step) of the decision apparatus, the learning apparatus, the determination apparatus, or the warning system described in the above-described example embodiments by causing a processor in a computer to execute a computer program.

Figure 20:
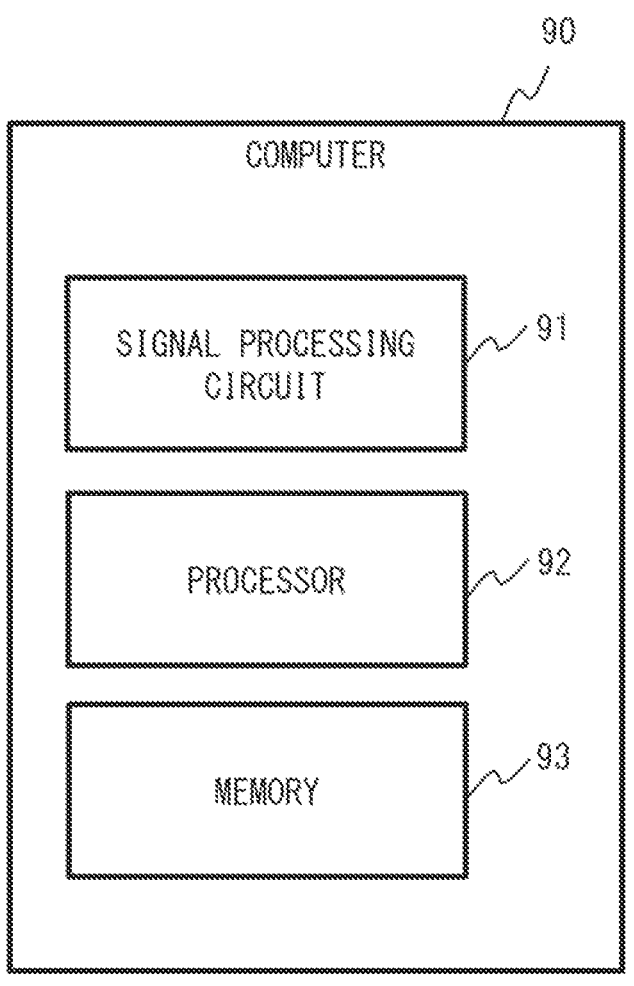
FIG. 20 is a block diagram illustrating one example of a hardware configuration of an apparatus according to the disclosure.

FIG. 20 is a block diagram illustrating a hardware configuration example of an information processing apparatus (signal processing apparatus) in which processing according to each of the above-described example embodiments is executed. Referring to FIG. 20, an information processing apparatus 90 includes a signal processing circuit 91, a processor 92, and a memory 93.

The signal processing circuit 91 is a circuit for processing a signal in response to control of the processor 92. Note that, the signal processing circuit 91 may include a communication circuit that receives a signal from a transmission apparatus.

The processor 92 is connected (coupled) to the memory 93, reads and executes software (a computer program) from the memory 93, and thereby performs processing of the apparatus described in the above-described example embodiments. As one example of the processor 92, one of a central processing unit (CPU), a micro processing unit (MPU), a field-programmable gate array (FPGA), a demand-side platform (DSP), and an application specific integrated circuit (ASIC) may be used, or a plurality of them may be used in parallel.

The memory 93 is configured by a volatile memory, a non-volatile memory, or a combination thereof. The number of memories 93 is not limited to one, and a plurality of memories may be provided. Note that, the volatile memory may be, for example, a random access memory (RAM) such as a dynamic random access memory (DRAM) or a static random access memory (SRAM). The non-volatile memory may be, for example, a read only memory (ROM) such as a programmable read only memory (PROM) or an erasable programmable read only memory (EPROM), a flash memory, or a solid state drive (SSD).

The memory 93 is used for storing one or more instructions. Herein, one or more instructions are stored in the memory 93 as a software module group. The processor 92 can read the software module group from the memory 93 and execute the read software module group, and thereby perform processing described in the above-described example embodiments.

Note that, the memory 93 may include one built in the processor 92, in addition to one provided outside the processor 92. In addition, the memory 93 may include a storage disposed away from a processor constituting the processor 92. In this case, the processor 92 can access the memory 93 via an input/output (I/O) interface.

As described above, one or a plurality of processors included in each of the apparatuses in the above-described example embodiments execute one or a plurality of programs including an instruction group for causing a computer to execute an algorithm described with reference to the drawings. By the processing, signal processing method described in each example embodiment can be achieved.

The program includes an instruction group (or a software code) that, when read to a computer, cause the computer to perform one or more of functions described in the example embodiments. The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), Blu-ray (registered trademark) Disc or other optical disk storage, optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), solid-state drive (SSD), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

The whole or part of the example embodiments disclosed above can be described as, but not limited to, the following supplementary notes.

(Supplementary Note 1)

A decision apparatus including:

a degree-of-necessity calculation unit configured to calculate a degree of necessity of generation of a document relating to a decision target person, by inputting state information of the decision target person with respect to a first learning model being learned by using first learning data including state information of a person and information indicating whether generation of the document relating to the person is necessary or unnecessary; and an alert decision unit configured to decide whether to output an alert related to document generation of the decision target person, by using the degree of necessity calculated by the degree-of-necessity calculation unit, and information indicating whether the document is actually generated for the decision target person.

(Supplementary note 2)

The decision apparatus according to supplementary note 1, wherein any of logistic regression, a support vector machine (SVM), and a neural network is used for learning the first learning model.

(Supplementary Note 3)

The decision apparatus according to supplementary note 1 or 2, wherein the degree-of-necessity calculation unit calculates, as the degree of necessity, a probability to be output by the first learning model or a value acquired by logit-converting the probability, which indicates at least any of necessary or unnecessary of generation of the document.

(Supplementary Note 4)

The decision apparatus according to any one of supplementary notes 1 to 3, wherein the alert decision unit outputs an alert related to document generation of the decision target person when the degree of necessity calculated by the degree-of-necessity calculation unit exceeds a predetermined threshold value and the document is not actually generated for the decision target person.

(Supplementary Note 5)

The decision apparatus according to any one of supplementary notes 1 to 4, wherein the alert decision unit predicts the degree of necessity at a future time point from a latest calculation time point for the decision target person, based on the degree of necessity calculated by the degree-of-necessity calculation unit at a latest calculation time point, and the past degree of necessity calculated by the degree-of-necessity calculation unit at a past time point from a latest calculation time point for the decision target person, and, when the predicted degree of necessity exceeds a predetermined threshold value, outputs an alert related to document generation of the decision target person.

(Supplementary Note 6)

The decision apparatus according to any one of supplementary notes 1 to 5, wherein state information of the person and state information of the decision target person include structured data and unstructured data subjected to preprocessing.

(Supplementary Note 7)

The decision apparatus according to any one of supplementary notes 1 to 6, further including a description content output unit configured to output a description content for each item in a document being necessary to be generated for the decision target person, by inputting state information of the decision target person with respect to a second learning model being learned by using second learning data including state information of the person and a description content for each item in a document generated for the person.

(Supplementary Note 8)

The decision apparatus according to any one of supplementary notes 1 to 7, wherein a document relating to the person is at least any of a document relating to a hospitalization treatment plan of the person, a document relating to a hospital infection prevention measure of the person, a document relating to a medical safety management system of the person, a document relating to a bedsore plan of the person, or a document relating to a nutritional management system of the person.

(Supplementary Note 9)

The decision apparatus according to any one of supplementary notes 1 to 8, wherein the alert decision unit extracts and presents information to be necessary for document generation of the decision target person from state information of the decision target person when outputting an alert related to document generation of the decision target person.

(Supplementary Note 10)

The decision apparatus according to any one of supplementary notes 1 to 9, further including a history presentation unit configured to present an output history of an alert related to document generation of the decision target person.

(Supplementary Note 11)

The decision apparatus according to any one of supplementary notes 1 to 10, wherein the alert decision unit changes a mode of the alert to be presented to a user, based on the degree of necessity calculated by the degree-of-necessity calculation unit.

(Supplementary Note 12)

The decision apparatus according to supplementary note 6, wherein the unstructured data are subjected to the preprocessing by any method of bag of words (BoW), Word2Vec, and bidirectional encoder representations from transformers (Bert), and are input to the first learning model.

(Supplementary Note 13)

A decision method being executed by a computer, the method including:

calculating a degree of necessity of generation of a document relating to a decision target person, by inputting state information of the decision target person with respect to a learning model being learned by using learning data including state information of a person and information indicating whether generation of the document relating to the person is necessary or unnecessary; and deciding whether to output an alert related to document generation of the decision target person, by using the calculated degree of necessity and information indicating whether the document is actually generated for the decision target person.

(Supplementary Note 14)

A program causing a computer to execute:

calculating a degree of necessity of generation of a document relating to a decision target person, by inputting state information of the decision target person with respect to a learning model being learned by using learning data including state information of a person and information indicating whether generation of the document relating to the person is necessary or unnecessary; and deciding whether to output an alert related to document generation of the decision target person, by using the calculated degree of necessity and information indicating whether the document is actually generated for the decision target person.

(Supplementary Note 15)

A learning apparatus including:

a preprocessing unit configured to generate state information of a person by performing preprocessing on data related to a state of the person; and a model learning unit configured to learn a model for calculating a degree of necessity of generation of a document relating to a decision target person, by using learning data including state information of the person and information indicating whether generation of the document relating to the person is necessary or unnecessary.

(Supplementary Note 16)

The learning apparatus according to supplementary note 15, wherein any of logistic regression, a support vector machine (SVM), and a neural network is used for learning the learning model.

(Supplementary Note 17)

The learning apparatus according to supplementary note 15 or 16, wherein a document relating to the person is at least any of a document relating to a hospitalization treatment plan of the person, a document relating to a hospital infection prevention measure of the person, a document relating to a medical safety management system of the person, a document relating to a bedsore plan of the person, or a document relating to a nutritional management system of the person.

(Supplementary Note 18)

The learning apparatus according to any one of supplementary notes 15 to 17, wherein state information of the person includes structured data and unstructured data being subjected to preprocessing.

(Supplementary Note 19)

The learning apparatus according to supplementary note 18, wherein the unstructured data are subjected to the preprocessing by any method of bag of words (BoW), Word2Vec, and bidirectional encoder representations from transformers (Bert), and are input to the learning model.

(Supplementary Note 20)

A learning method being executed by a computer, the method including:

generating state information of a person by performing preprocessing on data related to a state of the person; and learning a model for calculating a degree of necessity of generation of a document relating to a decision target person, by using learning data including state information of the person and information indicating whether generation of the document relating to the person is necessary or unnecessary.

(Supplementary Note 21)

A program causing a computer to execute:

generating state information of a person by performing preprocessing on data related to a state of the person; and learning a model for calculating a degree of necessity of generation of a document relating to a decision target person, by using learning data including state information of the person and information indicating whether generation of the document relating to the person is necessary or unnecessary.

One example of an advantageous effect according to the example embodiment of the present disclosure is that it is possible to provide a decision apparatus, a decision method, and a program that are useful for prompting to appropriately perform document generation relating to a decision target person.

While the disclosure has been particularly shown and described with reference to example embodiments thereof, the disclosure is not limited to these example embodiments. It will be understood by those of ordinary skill in the art that various changes in form and details may be made therein without departing from the spirit and scope of the present disclosure as defined by the claims.

What is claimed is:

1. A decision apparatus comprising:

at least one memory configured to store an instruction; and at least one processor configured to execute the instruction, wherein the processor, by executing the instruction, calculates a degree of necessity of generation of a document relating to a decision target person, by inputting state information of the decision target person with respect to a first learning model being learned by using first learning data including state information of a person and information indicating whether generation of the document relating to the person is necessary or unnecessary, and decides whether to output an alert related to document generation of the decision target person, by using the calculated degree of necessity and information indicating whether the document is actually generated for the decision target person, wherein the at least one processor executes the instruction, and thereby further predicts the degree of necessity at a future time point from a latest calculation time point for the decision target person, based on the degree of necessity calculated at a latest calculation time point, and the past degree of necessity calculated at a past time point from a latest calculation time point for the decision target person, and, when the predicted degree of necessity exceeds a predetermined threshold value, outputs an alert related to document generation of the decision target person.

2. The decision apparatus according to claim 1, wherein any of logistic regression, a support vector machine (SVM), and a neural network is used for learning the first learning model.

3. The decision apparatus according to claim 1, wherein the at least one processor executes the instruction, and thereby further calculates, as the degree of necessity, a probability to be output by the first learning model or a value acquired by logit-converting the probability, which indicates at least any of necessary or unnecessary of generation of the document.

4. The decision apparatus according to claim 1, wherein the at least one processor executes the instruction, and thereby further outputs an alert related to document generation of the decision target person when the calculated degree of necessity exceeds a predetermined threshold value and the document is not actually generated for the decision target person.

5. The decision apparatus according to claim 1, wherein state information of the person and state information of the decision target person include structured data and unstructured data being subjected to preprocessing.

6. The decision apparatus according to claim 1, wherein the at least one processor executes the instruction, and thereby further outputs a description content for each item in a document being necessary to be generated for the decision target person, by inputting state information of the decision target person with respect to a second learning model being learned by using second learning data including state information of the person and a description content for each item in a document generated for the person.

7. The decision apparatus according to claim 1, wherein a document relating to the person is at least any of a document relating to a hospitalization treatment plan of the person, a document relating to a hospital infection prevention measure of the person, a document relating to a medical safety management system of the person, a document relating to a bedsore plan of the person, or a document relating to a nutritional management system of the person.

8. The decision apparatus according to claim 1, wherein the at least one processor executes the instruction, and thereby further extracts and presents information to be necessary for document generation of the decision target person from state information of the decision target person when outputting an alert related to document generation of the decision target person.

9. The decision apparatus according to claim 1, wherein the at least one processor executes the instruction, and thereby further presents an output history of an alert related to document generation of the decision target person.

10. The decision apparatus according to claim 1, wherein the at least one processor executes the instruction, and thereby further changes a mode of the alert to be presented to a user, based on the calculated degree of necessity.

11. The decision apparatus according to claim 5, wherein the unstructured data are subjected to the preprocessing by any method of bag of words (BoW), Word2Vec, and bidirectional encoder representations from transformers (Bert), and are input to the first learning model.

12. A decision method being executed by a computer, the method comprising:

calculating a degree of necessity of generation of a document relating to a decision target person, by inputting state information of the decision target person with respect to a learning model being learned by using learning data including state information of a person and information indicating whether generation of the document relating to the person is necessary or unnecessary;

deciding whether to output an alert related to document generation of the decision target person, by using the calculated degree of necessity and information indicating whether the document is actually generated for the decision target person; and predicting the degree of necessity at a future time point from a latest calculation time point for the decision target person, based on the degree of necessity calculated at a latest calculation time point, and the past degree of necessity calculated at a past time point from a latest calculation time point for the decision target person, and, when the predicted degree of necessity exceeds a predetermined threshold value, outputting an alert related to document generation of the decision target person.

13. A non-transitory computer readable medium storing a program causing a computer to execute:

calculating a degree of necessity of generation of a document relating to a decision target person, by inputting state information of the decision target person with respect to a learning model being learned by using learning data including state information of a person and information indicating whether generation of the document relating to the person is necessary or unnecessary;

deciding whether to output an alert related to document generation of the decision target person, by using the calculated degree of necessity and information indicating whether the document is actually generated for the decision target person; and predicting the degree of necessity at a future time point from a latest calculation time point for the decision target person, based on the degree of necessity calculated at a latest calculation time point, and the past degree of necessity calculated at a past time point from a latest calculation time point for the decision target person, and, when the predicted degree of necessity exceeds a predetermined threshold value, outputting an alert related to document generation of the decision target person.

\* \* \* \* \*